(12) United States Patent
Hertzog et al.

(10) Patent No.: US 11,590,203 B2
(45) Date of Patent: Feb. 28, 2023

(54) METHOD OF TREATMENT OVARIAN CANCER

(71) Applicant: Hudson Institute of Medical Research, Clayton (AU)

(72) Inventors: Paul Hertzog, Tecoma (AU); Zoe Marks, West Footscray (AU); Nollaig Bourke, Kildare (IE); Sn Sui Lim, Keysborough (AU); Nicole De Weerd, Seaford (AU); Niamh Mangan, St. Kilda (AU); Antony Matthews, Chadstone (AU)

(73) Assignee: Hudson Institute of Medical Research, Victoria (AU)

( * ) Notice: Subject to any disclaimer, the term of this patent is extended or adjusted under 35 U.S.C. 154(b) by 233 days.

(21) Appl. No.: 16/482,081

(22) PCT Filed: Jan. 30, 2018

(86) PCT No.: PCT/AU2018/050054
§ 371 (c)(1),
(2) Date: Jul. 30, 2019

(87) PCT Pub. No.: WO2018/137002
PCT Pub. Date: Aug. 2, 2018

(65) Prior Publication Data
US 2019/0351025 A1    Nov. 21, 2019

(30) Foreign Application Priority Data

Jan. 30, 2017 (AU) .............................. 2017900251

(51) Int. Cl.
| | | |
|---|---|---|
| A61K 38/21 | (2006.01) | |
| C07K 14/555 | (2006.01) | |
| A61K 45/06 | (2006.01) | |

(52) U.S. Cl.
CPC ............ *A61K 38/21* (2013.01); *C07K 14/555* (2013.01); *A61K 45/06* (2013.01)

(58) Field of Classification Search
None
See application file for complete search history.

(56) References Cited

U.S. PATENT DOCUMENTS

| | | |
|---|---|---|
| 5,391,377 A | 2/1995 | Barnwell |
| 5,753,187 A | 5/1998 | Reynolds et al. |
| 5,763,263 A | 6/1998 | Dehlinger |
| 6,329,175 B1 | 12/2001 | Conklin et al. |

FOREIGN PATENT DOCUMENTS

| | | |
|---|---|---|
| WO | WO 1999/029863 | 6/1999 |
| WO | WO 2000/017361 | 3/2000 |

OTHER PUBLICATIONS

Alkema et al., Studying platinum sensitivity and resistance in high-grade serous ovarian cancer: Different model for different questions. Drug Resist. Updates, 24, 55-69, 2016. (Year: 2016).*
Altschul et al., "Gapped BLAST and PSI-BLAST: a new generation of protein database search programs," Nucl. Acids. Res., Sep. 2, 1997, 25(17):3389-3402.
AIHW, "Ovarian cancer in Australia," National Breast and Ovarian Cancer Centre (Australia), Feb. 2010, Cancer series 52, Cat No. CAN48, Front Mattter and Executive Summary.
Ausubel et al., "Sequence Similarity Searching Using the BLAST Family of Programs," Current Protocols in Molecular Biology, 1999, Supplement 46:19.3.1-19.3.29.
Berek et al., "Intraperitoneal recombinant alpha-interferon for "salvage" immunotherapy in stage III epithelial ovarian cancer: a Gynecologic Oncology Group Study," Cancer Res., Sep. 1985, 45(9):4447-4453.
Berek et al., "Intraperitoneal interferon-alpha in residual ovarian carcinoma: a phase II gynecologic oncology group study," Gynecol Oncol., Oct. 1999, 75(1):10-14.
Bowtell, "The genesis and evolution of high-grade serous ovarian cancer," Nature Rev Cancer, Nov. 2010, 10(11):803-808.
Bruzzone et al., "Intraperitoneal carboplatin with or without interferon-alpha in advanced ovarian cancer patients with minimal residual disease at second look: a prospective randomized trial of 111 patients. G.O.N.O, Gruppo Oncologic Nord Ovest," Gynecol Oncol., Jun. 1997, 65(3):499-505.
Bunin et al., "The combinatorial synthesis and chemical and biological evaluation of a 1,4-benzodiazepine libraiy," Proc. Natl. Acad. Sci. USA, May 24, 1994, 91(11):4708-4712.
Darnell "STATs and gene regulation," Science, Sep. 12, 1997, 277(5332):1630-1635.
Dewitt et al., "Diversomers": an approach to nonpeptide, nonoligomeric chemical diversity, Proc. Natl. Acad. Sci. USA, 90(15):6909-6913, 1993.
De Weerd et al., "Structural basis of a unique interferon-β signaling axis mediated via the receptor IFNAR1," Nat Immunol,, Sep. 2013, 14(9):901-907.
Domcke et al., "Evaluating cell lines as tumour models by comparison of genomic profiles," Nature Communications, 2013, 4:2126.
Egleton "Bioavailability and transport of peptides and peptide drugs into the brain," Peptides, 1997, 18(9):1431-1439.
Fix, "Oral controlled release technology for peptides: status and future prospects," Dec. 1996, Pharm Res. 13(12):1760-1764.
Frasci et al., "Carboplatin and alpha-2b interferon intraperitoneal combination as first-line treatment of minimal residual ovarian cancer. A pilot study," Eur. J. Cancer 1994, 30(7):946-950.
Fung et al., "Interferon & protects the female reproductive tract from viral and bacterial infection," Science, 2013, 339(6123):1088-1092.

(Continued)

*Primary Examiner* — Elly-Gerald Stoica
(74) *Attorney, Agent, or Firm* — Fish & Richardson P.C.

(57) ABSTRACT

The invention is directed to methods of treating cancers using Interferon-ε (IFN-ε), wherein the IFN-ε includes various natural, synthetic and recombinant IFN-ε in compositions.

18 Claims, 17 Drawing Sheets

Specification includes a Sequence Listing.

(56) References Cited

OTHER PUBLICATIONS

Gasteiger et al., "ExPASy: The proteomics server for in-depth protein knowledge and analysis," Nucleic Acids Res., Jul. 1, 2003, 31(13):3784-3788.
Greenaway et al., "Epithelial-stromal interaction increases cell proliferation, survival and tumorigenicity in a mouse model of human epithelial ovarian cancer," Gynecologic oncology, Feb. 2008, 108(2):385-394.
Hardy et al., "Characterization of the type I interferon locus and identification of novel genes," Genomics, Aug. 2004, 84(2):331-345.
International Search Report and Written Opinion in International Application No. PCT/AU2018/050054, dated Apr. 5, 2018, 10 pages.
Jaks et al., "Differential receptor subunit affinities of type I interferons govern differential signal activation," J Mol Biol., Feb. 16, 2007, 366(2):525-539.
Jayson et al., "Ovarian cancer," Lancet, Oct. 11, 2014, 384(9951):1376-1388.
Jaitin et al., "Inquiring into the differential action of interferons (IFNs): an IFN-alpha2 mutant with enhanced affinity to IFNAR1 is functionally similar to IFN-beta," Mol. Cell Biol., Mar. 2006, 26(5):1888-1897.
Kobolt et al., "Comprehensive molecular portraits of human breast tumours," Nature, Oct. 4, 2012, 490(7418):61-70.
Kurman and Shih, "Molecular pathogenesis and extraovarian origin of epithelial ovarian cancer—shifting the paradigm," Human pathology, Jul. 2011, 42(7):918-931.
Langer "New methods of drug delivery," Science, Sep. 28, 1990, 249(4976):1527-1533.
Mangan et al., "T1/ST2 expression on Th2 cells negatively regulates allergic pulmonary inflammation," Eur J Immunol., May 2007, 37(5):1302-1312.
Markman et al., "Characteristics of patients with small-volume residual ovarian cancer unresponsive to cisplatin-based ip chemotherapy: lessons learned from a Gynecologic Oncology Group phase II trial of ip cisplatin and recombinant alpha-interferon," Gynecol Oncol., Apr. 1992, 45(1):3-8.
Markman et al., "Phase 2 trial of interferon-beta as second-line treatment of ovarian cancer, fallopian tube cancer, or primary carcinoma of the peritoneum," Oncology, 2004, 66(5):343-346.
Moore et al., "A phase I study of intraperitoneal interferon-alpha 2b and intravenous cis-platinum plus cyclophosphamide chemotherapy in patients with untreated stage III epithelial ovarian cancer: a Gynecologic Oncology Group pilot study," Gynecol Oncol., Nov. 1995, 59(2):267-272.
Patch et al., "Whole-genome characterization of chemoresistant ovarian cancer," Nature, May 28, 2015, 521(7553):489-494.
Patton "Breathing life into protein drugs," Biotechniques, Feb. 1998, 16(2):141-143.
Peng et al. "Purification of recombinant human interferon-epsilon and oligonucleotide microarray analysis of interferon-epsilon-regulated genes," Prot Expr Purif., Jun. 2007, 53(2):356-362.
Putney "Improving protein therapeutics with sustained-release formulations," Nat. Biotechnol., Feb. 1998, 16(2):153-157.
Roby et al., "Development of a syngeneic mouse model for events related to ovarian cancer," Carcinogenesis, Apr. 2000, 21(4):585-591.
Salamonsen et al., "Cytokines and chemokines during human embryo implantation: roles in implantation and early placentation," Semin Reprod Med., Nov. 2007, 25(6):437-444.
Samanen "Chemical approaches to improve the oral bioavailability of peptidergic molecules," J. Pharm. Pharmacol., Feb. 1996, 48(2):119-135.
Sieh et al., "Hormone-receptor expression and ovarian cancer survival: an Ovarian Tumor Tissue Analysis consortium study," The Lancet Oncology, Aug. 2013, 14(9):853-862.
Smith et al., "Infection with a helminth parasite prevents experimental colitis via a macrophage-mediated mechanism," J Immunol., Apr. 1, 2007, 178(7):4557-4566.
Stifter et al., "Purification and biological characterization of soluble, recombinant mouse IFNβ expressed in insect cells," Protein Expr Purif., Feb. 2014, 94:7-14.
STN Search Report in Australian Application No. PCT/AU2018/05054, dated Apr. 5, 2018, 4 pages.
Tan et al., "CSIOVDB: a microarray gene expression database of epithelial ovarian cancer subtype," Oncotarget, Dec. 22, 2015, 6(41):43843-43852.
Thakkar and Mehta "A review of an unfavorable subset of breast cancer: estrogen receptor positive progesterone receptor negative," Oncologist, 2011, 16(3):276-285.
Tothill et al., "Novel molecular subtypes of serous and endometrioid ovarian cancer linked to clinical outcome," Clin Cancer Res., Aug. 15, 2008, 14(16):5198-5208.
Yang et al., "Molecular and Functional Characterization of Canine Interferon-Epsilon," Journal of Interferon & Cytokine Research, Aug. 15, 2013, 33(12):760-768.
Venkitaraman "Cancer suppression by the chromosome custodians, BRCA1 and BRCA2," Science, Mar. 28, 2014, 343(6178):1470-1475.
Willemse et al., "Intraperitoneal human recombinant interferon alpha-2b in minimal residual ovarian cancer," Eur. J. Cancer Clin. Oncol., Mar. 1990, 26(3):353-358.
Green et al., "Monocyte and interferon based therapy for the treatment of ovarian cancer," Cytokine & Growth Factor Reviews, 2016, 29:109-115.
Japanese Office Action in Japanese Application No. 2019-541256, dated Jan. 17, 2022, 12 pages (English translation).

\* cited by examiner hIFNe was expressed in bacteria: nucleotide (SEQ ID NO:27)
agatctgggtagcctggatctgaaactgattatctttcagcagcgtcaggttaatcaagaa
agcctgaaactgctgaataaactgcaaaccctgagcatcagcagtgtctgccgcatcgt
aaaaactttctgctgcctcagaaaagcctgagtccgcagcagtatcagaaaggtcatacc
ctggcaattctgcatgaaatgctgcaacaaatcttagctgtttcgtgcaaatattagt
ctggatggttgggaagaaaaccataccgaaaaatttctgattcagctgcaccagcagctg
gaatatctggaagcactgatgggtctggaagccgaaaaactgagcggtaccctgggtagc
gataatctgcgtctgcaagttaaaatgtatttcgtcgcatccacgactatctggaaaat
caggattatagcacctgtgcatgggcaattgttcaggttgaaattagccgttgcctgttt
tttgttttttagctgacagagaaactgagcaaacagggtcgtccgctgaatgatatgaaa
caagaactgaccaccgaatttcgtagtccgcgttctgcag protein translation (SEQ ID NO:28)
DLGSLDLKLIIFQQPQVNQESLKLLNKLQTLSISQQCLPHPKNFLLPQKSLSPQQYQKGHT
LAILHEMLQQIFSLFRANISLDGWEENHTEKFLIQLHQQLEYLEALMGLEAEKLSGTLGS
DNLRLQVKMYFRRIHDYLENQDYSTCAWAIVQVEISRCLFFVFSLTEKLSKQGPPLNDMK
QELTTEFRSPRSA Tagless mIFNe as was expressed in insect cells (SEQ ID NOs:29 and 30)

Figure 16A

Expression clone is: Nucleotide: (SEQ ID NO:31)
gccgaattggaaccaaagcgcatcccatttcagctgtggatgaaccgcgagagcctccagctccttaagccactgccctcctcgtc
agtgcagcagtgtctggcccaccgtaagaatttcctcctcccacaacagcccgtctcacctcatcaatatcaggagggtcaagtgct
ggctgtcgtgcatgagatcctgcagcaaatcttcacactgcttcagactcacggcactatgggtatttgggaggagaaccatatcga
gaaggtgctggctgccctccatcgtcagctggagtatgttgagagcctgggaggcctaaacgctgcccagaagtcaggcggctct
agtgcacagaacctgcgcttgcagatcaaggcttacttccgtcgcattcacgattacctggagaatcagcgctactctagctgtgcct
ggatcatcgttcaaaccgaaatccaccgttgtatgttcttcgtgttccgatttacgacctggctgtcacgccaagaccctgacccatga Protein translation: (SEQ ID NO:32)
AELEPKRIPFQLWMNRESLQLLKPLPSSVQQCLAHRKNFLLPQQPVSPHQYQEGQVLAV
VHEILQQIFTLLQTHGTMGIWEENHIEKVLAALHRQLEYVESLGGLNAAQKSGGSSAQNL
RLQIKAYFRRIRDYLENQRYSSCAWIIVQTEIHRCMFFVFRFTTWLSPQDPDP

Figure 16B

METHOD OF TREATMENT OVARIAN CANCER

This application is the National Stage of International Patent Application No. PCT/AU2018/050054, filed on Jan. 30, 2018, which claims priority to Australian Provisional Patent Application No. 2017900251, filed on Jan. 30, 2017, entitled "A method of treatment", the entire contents of which, are incorporated herein by reference, in their entirety. This specification refers to a Sequence Listing. The "ST25.txt" file is in ANSI format. The file is hereby incorporated in its entirety by reference from AU 2017900251 into the subject specification.

FIELD

The present invention relates to the field of cancer treatment and formulations useful for same.

BACKGROUND

Bibliographic details of the publications referred to by author in this specification are collected alphabetically at the end of the description.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavor to which this specification relates.

Cancer is a complex, multifaceted, cellular disorder. It can lead to debilitating levels of disease with potentially significant morbidity and mortality rates. The economic cost to the healthcare sector in the treatment of cancer, not to mention the emotional burden to individuals and families, is substantial. Much effort has been invested in understanding cancer biology and endogenous and exogenous factors which retard its development. Despite great advances over the decades, further research is crucial in order to fully understand this disease.

Ovarian cancer, for example, is a complex, heterogeneous disease comprising a number of molecularly distinct tumors that arise not only from ovarian cells but also cells of the fallopian tubes and/or surrounding tissue (Jayson et al. (2014) *The Lancet* 384(9951):1376-88). Many women are first diagnosed when they already have reached advanced stage disease and of those who respond to treatment, more than half will relapse and die within 5 years (AIHW. (2010) *Cancer series* 52 Cat No. CAN48).

The vast majority of ovarian cancers are of epithelial origin (EOC) and have the fourth highest female cancer fatality rate (Jayson et al. (2014) supra). EOC is classified based on histological subtype including mucinous, clear cell, endometroid and serous carcinomas, each of which is associated with a distinct morphology, mutational profile, cell of origin and prognosis. Serous carcinomas are the most commonly diagnosed EOC and there is increasing evidence to suggest that EOC is derived from the secretory epithelial lining of the distal fallopian tube. The standard therapeutic options, surgical resection and platinum-based chemotherapy, are often ineffective as many women with advanced disease are not surgical candidates and chemoresistence leads to increasing rates of recurrence (Jayson et al. (2014) supra).

Extensive molecular profiling of ovarian cancers has shown that mutations in BRCA1/2 genes confer significantly increased risk of high-grade serous carcinoma (HGSC), the most common and lethal EOC (Bowtell et al. (2010) *Nature Rev Cancer* 10(11):803-8). BRCA1 and BRCA2 are both documented interferon (IFN) regulated genes (IRGs) and play an important role in the homologous recombination repair pathway of DNA (Venkitaraman (2014) *Science* 343(6178):1470-5), somatic and germline mutations of which contribute to overall chromosomal instability. Molecular profiling has also identified that high grade serous carcinoma (HGSC) with higher expression of immune-associated genes such as CD8A, Granzyme B and CXCL9, designated the immunologic subtype, demonstrate the best overall survival (Tothill et al. (2008) *Clin Cancer Res.* 14(16):5198-208), highlighting the potential benefit of immune-driven suppression in this cancer, Molecular profiling has identified similarities in the mutational profile of basal-like breast cancers and serous ovarian cancers with high frequency TP53, BRCA1 and BRCA2 mutations, down-regulation of RB1 and amplification of cyclin E1 common to both (Kobolt et al. (2012) *Nature* 490(7418): 61-70). Additionally, while the role of hormones in ovarian cancer tumorigenesis remains unclear, there is evidence of poor prognosis in progesterone receptor (PR) negative patients irrespective of estrogen receptor (ER) expression (Sieh et al. (2013) *The Lancet Oncology* 14(9):853-62), which bears similarities to the reports of poor prognosis in breast cancer patients with either triple negative breast cancer (TNBC) or estrogen receptor positive/progesterone receptor negative ($ER^+/PR^-$) cancers (Thakkar and Mehta (2011) *Oncologist* 16(3):276-85). Much is still unknown about the common drivers in these two cancers, both have common elements of oncogene and tumor suppressor gene expression, hormone sensitivity and immune cell involvement.

There is a need to further examine the effect of immune induction in regulating the development and treatment of ovarian cancer as well as other cancer types.

This is particularly the case with respect to the interplay between innate and adaptive immunity. The innate immune response represents pre-existing, inherent, first line and rapidly inducible defense to pathogens and responses to homeostatic cues (Mangan et al. (2007) *Eur J Immunol* 37(5):1302-12; Smith et al. (2007) *J Immunol* 178(7):4557-66). This is mediated through resident cells such as macrophages, natural killer (NK) and epithelial cells. Adaptive immune responses encompass the recognition, and response to antigens with elicited responses being gradual and specific, mediated through antibody secreting B lymphocytes and T helper and effector lymphocytes. The adaptive response is sculpted by the innate system. In the reproductive tract, both arms of the immune system must balance the presence of an allogenic fetus, essentially containing "foreign" proteins, with the control of harmful pathogens e.g. viruses and bacteria. It must also maintain homeostasis against a background of cyclical hormonal milieu and structural changes that occur in the mucosa.

The innate and adaptive immune cells of the female reproductive tract (FRT) produce cytokines and chemokines, thereby influencing various reproductive processes including sperm migration, fertilization, implantation, endometrial remodeling and immune response to infectious or other challenge (Salamonsen et al. (2007) *Semin Reprod Med* 25(6):437-44).

In its simplest form, the innate response includes physicochemical barriers such as mucous secretions, pH and redox state. In its most sophisticated form it is represented by the innate immune response which senses pathogens within minutes and starts a series of reactions, culminating in the production of products like antimicrobial defensins, NOS enzymes, chemokines that recruit and activate inflammatory cells and cytokines that modulate cell behavior. One family of inducers having pleiotropic activity is the type I interferons (IFNs).

Clinical trials for the treatment of ovarian cancer using type I IFNs, specifically IFNα and IFNβ have been underwhelming, largely due to the dose-limiting toxicity preventing high-dose therapy in late stage disease as is the case with other solid tumors (Berek et al. (1985) *Cancer Res.* 45:4447-53; Willemse et al. (1990) *Eur J Cancer Clin Oncol* 26(3): 353-8; Markman et al. (1992) *Gynecol Oncol.* 45(1):3-8; Frasci et al. (1994) *Eur J Cancer* 30(7):946-50; Bruzzone et al. (1997) *Gynecol Oncol.* 65(3):499-505; Moore et al. (1995) *Gynecol Oncol.* 59(2):267-72; Berek et al. (1999) *Gynecol Oncol.* 75(1):10-4; Markman et al. (2004) *Oncology* 66(5):343-6). Some success, however, has been reported using intraperitoneal IFNα in the treatment of malignancy ascites from ovarian cancer notwithstanding that the mechanisms underlying IFN's efficacy against ascites remain unclear (Berek et al. (1985) *Cancer Res.* 45:4447-53). It is important to understand the role of IFNs in disease pathogenesis in order to best direct therapy.

IFN epsilon (IFNε) is a type I IFN (Fung et al. (2013) *Science* 339(123):1088-1092; Peng et al. (2007) *Prot Expr Purif* 53(2):356-362). The Ifnε gene is located on chromosome 9p in the type I IFN locus (Hardy et al. (2004) *Genomics* 84(2):331-45). IFN shares roughly 30% amino acid sequence homology with IFNα and IFNβ, and in vitro studies demonstrated that IFNε signals through the characteristic type I IFN receptors 1FNAR1 and 1FNAR2, however, its potential anti-tumor properties have hitherto not been addressed.

Interestingly, unlike other type I IFNs which remain at undetectable levels until pathogen-induced, IFNε has been found to be constitutively expressed primarily in organs of the FRT such as uterus, cervix vagina and ovary. IFNε is produced by luminal and glandular epithelial cells of the FRT and is unaltered in the absence of hemopoietic cells.

Additionally, regulation of IFNε is distinct from other type I IFNs. Unlike Ifnα and Ifnβ, murine Ifnε expression is largely unaltered in response to pathogenic stimuli Instead, IFNε levels vary significantly across stages of the murine estrous cycle, with expression levels 30-fold higher during estrus than diestrus, an expression pattern that is reflected in human tissue during the menstrual cycle. This indicates that unlike other type I IFNs, IFNε is hormonally regulated.

There is a need to investigate the role of IFNε in cancer biology.

SUMMARY

Nucleotide and amino acid sequences are referred to by a sequence identifier number (SEQ ID NO). The SEQ ID NOs correspond numerically to the sequence identifiers <400>1 (SEQ ID NO:1), <400>2 (SEQ ID NO:2), etc. A summary of the sequence identifiers is provided in Table 2. A sequence listing is provided after the claims.

The present invention is predicated in part on the determination that IFNε has a role in inhibiting cancer cells. Such an inhibition includes directly or indirectly inducing cancer cell death, including by apoptotic processes, as well as arresting including slowing or inhibiting development, proliferation, motility and/or migration of cancer cells. IFNε may act directly on the cancer cell or it may induce an immune response that act via particular cell types or production of regulators or other factors which in turn induce a cytotoxic or cytostatic effect on cancer cells, or via cells of the stroma or components of the environment of the tumor cell. Whilst the present invention was elucidated following an investigation of ovarian cancer, the findings apply to other cancers of the female reproductive tract (FRT) as well as cancers elsewhere in the body of female or male subjects in any mammals, in particular, humans.

Hence, the present invention provides a method for inhibiting viability, growth, development and spread of cancer cells in a subject including a human. This encompasses arresting including slowing or inhibiting development, proliferation, motility and migration of cancer cells.

Accordingly, taught herein is a method for inhibiting a cancer cell in a subject, the method comprising exposing the cancer cell to an amount of interferon epsilon (IFNε) or a functional natural or synthetic variant or hybrid form thereof or an inducer of Ifnε expression or IFNε activity effective to directly or indirectly induce apoptosis of the cancer cell or inhibit cancer cell proliferation, motility and/or migration. This can lead to a reduction in the localized growth and invasion of cancer cells as well as their metastasis to other parts of the body. By "exposing" in relation to cancer cells, means directly or indirectly exposing cancer cells or via other cells or components.

Further enabled herein is a method for treating a subject with cancer, the method comprising administering to the subject an effective amount of IFNε or a functional natural or synthetic variant or hybrid form thereof or an inducer of Ifnε expression or IFNε activity for a time and under conditions sufficient to directly or indirectly induce apoptosis of cancer cells or inhibit cancer cell proliferation, motility and/or mitigation. This includes arresting cancer cell growth and development.

The present specification is instructional on the use of IFNε or a functional natural or synthetic variant or hybrid form thereof or an inducer of Ifnε expression or IFNε activity in the manufacture of a medicament in the treatment of cancer in a subject. In an embodiment, taught herein is IFNε or a functional natural or synthetic variant or hybrid form thereof or an inducer of Ifnε expression or IFNε activity for use in the treatment of cancer in a subject. The medicament includes an anti-cancer vaccine comprising IFNε or its variant or hybrid or inducer as the primary active ingredient or where it acts as an adjuvant for another anti-cancer agent. Examples of other anti-cancer agents which may be used in conjunction with IFNε or its variant or hybrid or inducer include chemotherapeutic agents, antimetabolites, anti-tumor antibiotics, mitotic inhibitors, steroids, sex hormones or hormone-like drugs, alkylating agents, nitrogen mustard, nitrosoureas, hormone agonists and microtubular inhibitors. Recombinant cells may also be engineered to produce IFNε or its variant, hybrid or inducer or recombinant viruses engineered to direct infected cells to produce IFNε, its variant, hybrid or inducer. Engineered IFNε includes an IFNε produced by optimized codon expression and/or optimized therapeutic activity.

Formulations comprising IFNε or a functional natural or synthetic variant or hybrid form thereof or an inducer of Ifnε expression or IFNε activity and one or more carriers, adjuvants and/or excipients for use in the treatment of cancer.

The IFNε or its functional natural or synthetic variant or hybrid form thereof may also be used as a vaccine adjuvant in conjunction with an anti-cancer agent or cancer cell regulating molecules.

Abbreviations used herein are defined in Table 1.

TABLE 1

Abbreviations

| Abbreviation | Definition |
|---|---|
| EOC | Epithelial origin |
| ER | Estrogen receptor |
| FCS | Fetal calf serum |
| FRT | Female reproductive tract |
| HGSC | High grade serous carcinoma |
| HuIFNε | Human interferon epsilon |
| IFN | Interferon |
| IFNε | Interferon epsilon |
| IRG | Interferon regulated gene |
| Ifnε | Gene encoding IFNε |
| LGSC | Low grade serous carcinoma |
| MuIFNε | Mouse interferon epsilon |
| PEC | Peritoneal exudate cells |
| PR | Progesterone receptor |
| TNBC | Triple negative breast cancer |

BRIEF DESCRIPTION OF THE FIGURES

Some figures contain color representations or entities. Color photographs are available from the Patentee upon request or from an appropriate Patent Office. A fee may be imposed if obtained from a Patent Office.

FIGS. 16A and B are representations of nucleotide and amino acid sequences of human and murine IFNε including optimized expression sequences (optimized codon usage).

DETAILED DESCRIPTION

Figure 1:
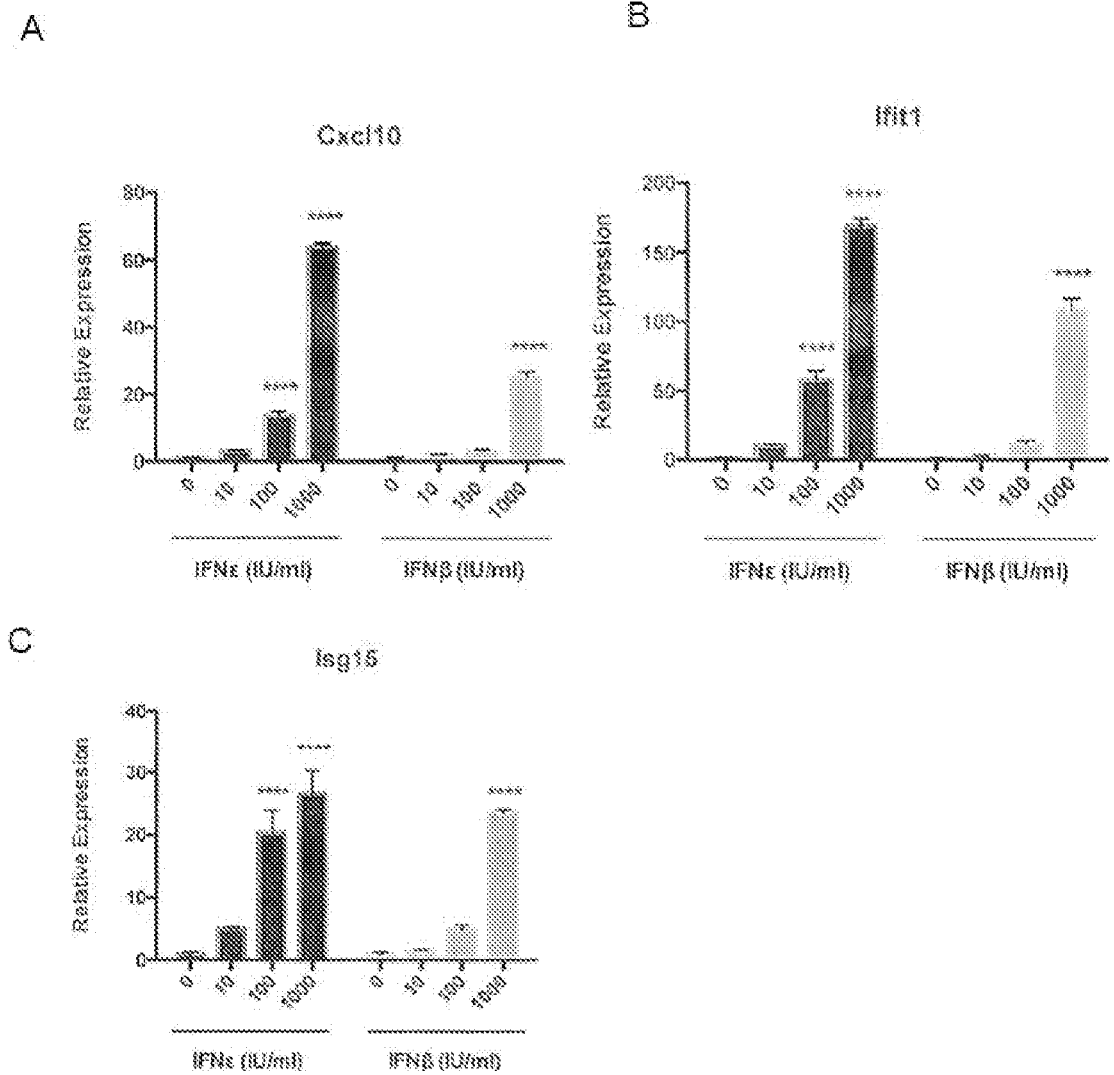
FIGS. 1A through C are graphical representations showing induction of interferon regulating genes (IRGs) in ID8 cells by IFNε and IFNβ. The graphs show a 3 hour dose response of 10-1000 IU/ml IFNε (left panels shown in black) and IFNβ (right panels in grey) induction of CXCL10 (A), Ifit1 (B) and Isg15 (C). Gene expression is measured by qRT-PCR, expression calculated by dCT standardized to 18 s and relative expression shown here determined in relation to expression at t0. Data are shown as mean+/−SEM of n=3 independent experiments, each done in technical triplicates. Significance was determined by Student's T test ****p<0.0001.

Throughout this specification, unless the context requires otherwise, the word "comprise", or variations such as "comprises" or "comprising", will be understood to imply the inclusion of a stated element or integer or method step or group of elements or integers or method steps but not the exclusion of any other element or integer or method steps or group of elements or integers or method steps.

As used in the subject specification, the singular forms "a", "an" and "the" include plural aspects unless the context clearly dictates otherwise. Thus, for example, reference to "a cancer cell" includes a single cancer cell, as well as two or more cancer cells; reference to "an IFNε" includes a single IFNε molecule, as well as two or more IFNε molecules; reference to "the disclosure" includes single and multiple aspects taught by the disclosure; and so forth. Aspects taught and enabled herein are encompassed by the term "invention". Any variants and derivatives contemplated herein are encompassed by "forms" of the invention. All aspects of the invention are enabled across the width of the claims.

The present invention teaches the use of interferon epsilon (IFNε) in the treatment of cancer in a subject. This includes a functional natural or synthetic variant or hybrid form of IFNε. Further taught herein is the use of an inducer of Ifnε expression or IFNε activity in the treatment of cancer. Hence, IFNε or its functional natural or synthetic variant or hybrid form may act directly on a cancer cell or may act indirectly via innate or adaptive immune cells or regulators or processes induced by IFNε or via cells of the stroma or components of the environment of the tumor cell.

Hence, enabled herein is the use of:

(i) natural purified IFNε;

(ii) recombinant IFNε, including IFNε produced by optimized expression;

(iii) a functional natural variant of IFNε;

(iv) a functional synthetic variant of IFNε, including optimized for activity;

(v) a hybrid of two or more IFNε from different species; and/or (vi) an inducer of Ifnε expression or IFNε activity, to directly or indirectly inhibit a cancer cell. The present invention may use any one of (i) through (vi), that is an agent selected from the group consisting of (i) through (vi), or use combination of two or more of (i) through (vi) to treat cancer. Reference to an inducer of Ifnε expression or IFNε activity includes an agent which up-regulates promoter activity, optimizes regulatory control to provide elevated levels of IFNε and agents which enhance IFNε activity.

The treatment of cancer comprises the inhibition of a single or multiple cancer cells. This comprises any one or more of directly or indirectly inducing apoptosis of a cancer cell, directly or indirectly acting as a cytotoxic agent, directly or indirectly inhibiting replication, growth, development, motility, proliferation, survival and/or migration of a cancer cell and/or directly or indirectly inducing cytostasis of a cancer cell. The treatment may enhance anti-cancer activity via cells of the stroma or components of the environment of the tumor cell.

In addition, the IFNε or its functional natural or synthetic variant or inducer may directly or indirectly prevent localized growth or invasion of a cancer cell and/or prevent metastasis of cancer cells elsewhere in the body of a subject including regions distant to the original foci of cancer cell development.

The present invention arose in part from an investigation of ovarian cancer. However, the anti-cancer effects of IFNε are applicable to any of a range of cancers including cancers derived from epithelial tissue, connective tissue, glandular tissue, embryonic tissue, blood borne cancers and cancers comprising hemopoietic cells, lymphatic tissue and bone marrow or cells from which such cells are derived. The present invention is not to be limited to the treatment of any one type of cancer or organ or anatomical compartment or region affected by cancer. Hence, the present invention extends to the treatment of cancers from any of the ovary, uterus, fallopian tube, endometrium, placenta, breast, testis, prostate, brain, stomach, liver, spleen, pancreas, thymus, colon, lung, kidney, heart, thyroid and smooth muscle. This is not intended to be an exhaustive list but representative of the types of cancers that can be treated by IFNε or a functional natural or synthetic variant or hybrid thereof or an inducer of Ifnε expression or IFNε activity.

In an embodiment, however, the present invention extends to cancer affecting the female reproductive tract (FRT) such as but not limited to ovarian cancer. As indicated above, the IFNε or its functional natural or synthetic variant or hybrid form may act directly on a cancer cell inducing any one or more of apoptosis, cytoxicity, senescence, lysis or other form of cell death or may retard, inhibit or otherwise inhibit cell growth, proliferation, replication, development, migration or motility. The IFNε or its functional natural or synthetic variant or hybrid form may also act indirectly on a cancer cell inducing any one or more of apoptosis, cytoxicity, senescence, lysis or other form of cell death or may retard, inhibit or otherwise arrest cell growth, proliferation, replication, development, migration or motility. Without limiting the present invention to any theory or mode of action, indirect activity includes the induction of innate and adaptive immune regulators and processes. The IFNε may also act via cells of the stroma or components in the environment surrounding the cancer cells or cancer tissue.

The subject being treated includes a human and a non-human mammal. Non-human animals include those useful in animal models. Such animals include mice, rats, guinea pigs, hamsters, rabbits, pigs and larger non-human animals. Other animals encompassed herein are companion animals (e.g. dogs and cats) and equine animals including a horse, a Przewalski horse, a zebra and an ass. A "horse" includes a Thoroughbred, a Warmblood, a Quarter horse and a Standardbred horse. Captive wild animals such as the Tasmanian devil, may also be subject of treatment and are encompassed by the present invention. Hence, the present invention has applications in human and veterinary medicine and as a research tool.

Reference to a human subject includes a human of any gender or age. In an embodiment, the human is a female with a cancer affecting the FRT such as but not limited to ovarian cancer.

Whilst not intending to limit the scope of the present invention to any type of cancer, it extends to carcinoma, sarcoma, adenocarcinoma, blastoma, leukemia, lymphoma and myeloma. The term "cancer" is not to be construed as distinguish from a "tumor" and both terms are used herein to mean the same cell type. A cancer may be of any grade and any stage, regardless of how the staging is classified. Hence, the cancer may be a solid tumor or blood or lymph fluid borne or bone marrow derived and may be defined in terms of cell type, location, tumor size, degree of local, regional or distant metastasis. For example, in relation to ovarian cancer, this may be serous, mucinous, clear cell or endometroid of high grade or low grade or a grade inbetween.

Accordingly, enabled herein is a method for inhibiting a cancer cell in a subject, the method comprising exposing the cancer cell to an amount of interferon epsilon (IFNε) or a functional natural or synthetic variant or hybrid form thereof or an inducer of Ifnε expression or IFNε activity effective to indirectly or indirectly induce apoptosis of the cancer cell survival, proliferation, motility and/or migration.

Further enabled herein is a method for treating a subject with cancer, the method comprising administering to the subject an effective amount of IFNε or a functional natural or synthetic variant or hybrid form thereof or an inducer of Ifnε expression or IFNε activity for a time and under conditions sufficient to induce apoptosis of cancer cells or inhibit cancer cell proliferation motility and/or migration.

Taught herein is the use of IFNε or a functional natural or synthetic variant or hybrid form thereof or an inducer of Ifnε expression or IFNε activity in the manufacture of a medicament in the treatment of cancer in a subject.

Further taught herein is IFNε or a functional natural or synthetic variant or hybrid form thereof or an inducer of Ifnε expression or IFNε activity for use in the treatment of cancer in a subject.

The IFNε or its functional natural or synthetic variant or hybrid form may also be employed as an adjuvant for use with an anti-cancer agent such as a chemotherapeutic agent, another type I interferon such as IFNα or IFNβ or another biological molecule. By "adjuvant" in this context means that the IFNε or variant or hybrid acts in synergy with another anti-cancer agent.

Hence, enabled herein is a method for inhibiting a cancer cell in a subject, the method comprising exposing the cancer cell with an amount of interferon epsilon (IFNε) or a functional natural or synthetic variant or hybrid form thereof or an inducer of Ifnε expression or IFNε activity in combination with another anti-cancer agent effective to indirectly or indirectly induce apoptosis of the cancer cell survival, proliferation, motility and/or migration.

Further enabled herein is a method for treating a subject with cancer, the method comprising administering to the subject an effective amount of IFNε or a functional natural or synthetic variant or hybrid form thereof or an inducer of Ifnε expression or IFNε activity in combination with another anti-cancer agent for a time and under conditions sufficient to induce apoptosis of cancer cells or inhibit cancer cell proliferation motility and/or migration.

Taught herein is the use of IFNε or a functional natural or synthetic variant or hybrid form thereof or an inducer of Ifnε expression or IFNε activity in combination with another anti-cancer agent in the manufacture of a medicament in the treatment of cancer in a subject. The medicament may be a single entity or a collocation of pharmaceutically effective agents which are used in combination with each other.

Reference to another anti-cancer agent includes but is not limited to a chemotherapeutic agent, an antimetabolite, an antitumor antibolite, a mitototoxic inhibitor, a steroid, a sex hormone or hormone-like drug, an alkylating agent, nitrogen mustard, nitrosourea, and/or a hormone agonist. The anti-cancer agent may further comprise microtubular immune cells or product thereof.

Examples of chemotherapeutic agents include dactinomycin, daunorubicin, doxorubicin (Adriamycin), idarubicin and mitoxantrone, or platinum based agents. Antimetabolites are substances that interfere with the body's chemical processes, such as creating proteins, DNA, and other chemicals needed for cell growth and reproduction; in cancer treatment, antimetabolite drugs disrupt DNA production, which in turn prevents cell division. Examples include Azaserine, D-Cycloserine, Mycophenolic acid, Trimethoprim, 5-fluorouracil, capecitabine, methotrexate, gemcitabine, cytarabine (ara-C) and fludarabine.

Antitumor antibiotics interfere with DNA by stopping enzymes and mitosis or altering the membranes that surround cells. These agents work in all phases of the cell cycle. Thus, they are widely used for a variety of cancers. Examples of antitumor antibiotics include dactinomycin, daunorubicin, doxorubicin (Adriamycin), idarubicin, and mitoxantrone.

Mitotic inhibitors are plant alkaloids and other compounds derived from natural products. They can inhibit, or stop, mitosis or inhibit enzymes for making proteins needed for reproduction of the cell. These work during the M phase of the cell cycle. Examples of mitotic inhibitors include paclitaxel, docetaxel, etoposide (VP-16), vinblastine, vincristine, and vinorelbine.

Steroids are natural and synthetic hormones that are useful in treating some types of cancer (lymphoma, leukemias, and multiple myeloma) as well as other illnesses. They can kill cancer cells or slow their growth. Examples include prednisone and dexamethasone.

Sex hormones, or hormone-like drugs, alter the action or production of female or male hormones. They are used to slow the growth of breast, prostate, and endometrial cancers, which normally grow in response to hormone levels in the body. Examples include anti-estrogens (tamoxifen, fulvestrant), aromatase inhibitors (anastrozole, letrozole), progestins (megestrol acetate), anti-androgens (bicalutamide, flutamide), and LHRH agonists (leuprolide, goserelin).

Alkylating agents work directly on DNA to prevent the cancer cell from reproducing. As a class of drugs, these agents are not phase-specific (in other words, they work in all phases of the cell cycle). These drugs are active against chronic leukemias, non-Hodgkin's lymphoma, Hodgkin's disease, multiple myeloma, and certain cancers of the lung, breast, and ovary. Examples of alkylating agents include busulfan, cisplatin, carboplatin, chlorambucil, cyclophosphamide, ifosfamide, dacarbazine (DTIC), mechlorethamine (nitrogen mustard), and melphalan.

Nitrogen mustard in the form of its crystalline hydrochloride it is used as a drug in the treatment of Hodgkin's disease, non-Hodgkin's lymphomas, and brain tumors. Nitrogen mustards cause mutations in the genetic material of cells, thereby disrupting mitosis, or cell division. Cells vary in their susceptibility to nitrogen mustards, with rapidly proliferating tumor and cancer cells most sensitive; bone marrow, which produces red blood cells, is also sensitive, and depression of red blood cell production is a frequent side effect of nitrogen mustard therapy. The nitrogen mustards also suppress the immune response (see immunity). Other types include the aromatic mustards melphalan and chlorambucil, cyclophosphamide, HN1, bis-(2-chloroethyl), ethylamine; HN2, bis-(2-chloroethyl), methylamine and HN3, tris-(2-chloroethyl), amine.

Nitrosoureas act in a similar way to alkylating agents. They interfere with enzymes that help repair DNA. These agents are able to travel to the brain so they are used to treat brain tumors as well as non-Hodgkin's lymphomas, multiple myeloma, and malignant melanoma. Examples of nitrosoureas include carmustine (BCNU) and lomustine (CCNU).

Hormone agonists include leuprolide (Lupron, Viadur, Eligard) for prostate cancer, Goserelin (Zoladex) for breast and prostate cancers and Triptorelin (Trelstar) for ovarian and prostate cancers and nafarelin acetate (Synarel).

Microtubule inhibitors include "Vinca" alkaloids, taxoids and benzimidazoles

Inducing Ifnε expression or IFNε activity includes the use of IFNε inducer agents. Such agents include proteinaceous and non-proteinaceous agents. These agents may interact with regulatory regions for the gene (including mature or precursor forms of IFNε) or modulate the expression of an upstream molecule, which upstream molecule subsequently modulates Ifnε expression or expression product activity. Accordingly, contemplated herein are agents which either directly or indirectly induce or modify Ifnε expression and/or IFNε activity.

Without limiting the present invention in any way, Ifnε expression is known to be hormonally regulated. Accordingly, in one embodiment the use of estrogen and estrogen mimetics provides a useful means of upregulating IFNε levels. In another example, TGFβ can be utilized. Similarly bioinformatic analysis has identified glucocorticoid receptor response elements and Ets factor binding elements within the IFNε promoter. The putative transcription factor binding site for BRCA1 has also been identified in the human Ifnε promoter. Accordingly, molecules which activate transcription via these sites, such as Elf3 and Elf5, could be utilized to upregulate Ifnε expression.

The inducer agents which are utilized in accordance with this aspect of the present invention may take any suitable form. For example, proteinaceous agents may be glycosylated or unglycosylated, phosphorylated or dephosphorylated to various degrees and/or may contain a range of other molecules used, linked, bound or otherwise associated with the proteins such as amino acids, lipid, carbohydrates or other peptides, polypeptides or proteins. Similarly, non-proteinaceous molecules may also take any suitable form. Both the proteinaceous and non-proteinaceous agents herein described may be linked, bound otherwise associated with any other proteinaceous or non-proteinaceous molecules.

For example, in one embodiment of the present invention the agent is associated with a molecule which permits its targeting to a localized region.

The term "expression" refers to the transcription and/or translation of a nucleic acid molecule. Reference to "expression product" is a reference to the product produced from the transcription and translation of a nucleic acid molecule.

"Variants" of the molecules herein described include fragments, parts, portions or derivatives either naturally occurring or synthetically prepared. Non-natural sources include, for example, recombinant or synthetic sources. By "recombinant sources" is meant that the cellular source from which the IFNε is harvested has been genetically altered. This may occur, for example, in order to increase or otherwise enhance the rate and volume of production by that particular cellular source. Parts or fragments include, for example, active regions of IFNε. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence. Substitutional amino acid variants are those in which at least one residue in a sequence has been removed and a different residue inserted in its place. Additions to amino acid sequences include fusions with other peptides, polypeptides or proteins, as detailed above.

Variants also include fragments having particular epitopes or parts of the entire IFNε protein fused to peptides, polypeptides or other proteinaceous or non-proteinaceous molecules. Analogs of the molecules contemplated herein include, but are not limited to, glycosylation variants, modification to side chains, incorporating of unnatural amino acids and/or their derivatives during peptide, polypeptide or protein synthesis and the use of crosslinkers and other methods which impose conformational constraints on the proteinaceous molecules or their analogs.

A "variant" or "mutant" of IFNε should be understood to mean molecules which exhibit at least some of the functional activity of IFNε (i.e. direct or indirect anti-cancer activity) of which it is a variant or mutant. A variation or mutation may take any form and may be naturally or non-naturally occurring. In an embodiment, the nucleic acid has undergone codon optimization to enhance expression and/or the IFNε protein may contain amino acid changes in order to optimize activity. In an embodiment, the variant is a hybrid of two or more IFNε molecules. For example, an IFNε derived from the species of the subject being treated may be modified to incorporate aspects of an IFNε from another species or vice versa. In one example, murine IFNε can have greater activity on human cells than human IFNε. Hence, a hybrid murine IFNε which incorporates elements of human IFNε to render it non-immunogenic (or vice versa) may be generated.

Reference to an IFNε or its nucleic acid includes a protein sequence having at least 80% similarity to SEQ ID NOs:28 or 32 or at least 80% identity to SEQ ID NOs:27, 29 or 31. Reference to at least "80%" includes 80, 81, 82, 83, 84, 85, 86, 87, 88, 89, 90, 91, 92, 93, 94, 95, 96, 97, 98, 99 or 100%. Variants of nucleic acids encoding IFNε include nucleic acids which hybridize under low stringency conditions to the complement of SEQ ID NOs:27, 29 or 31 under low stringency conditions (see also FIG. 16).

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In an embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al. (1997) *Nucl. Acids. Res.* 25:3389. A detailed discussion of sequence analysis can be found in Unit 19.3 of Ausubel et al. (*In: Current Protocols in Molecular Biology*, John Wiley & Sons Inc. 1994-1998).

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Be, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

The present invention extends to variants of the Ifnε nucleic acid molecules. Generally, a variant will still hybridize to a Ifnε sequence under low stringency conditions.

Variants include chemical and functional equivalents of IFNε which include molecules exhibiting any one or more of the functional activities (i.e. direct or indirect anti-cancer activity) of the IFNε, which functional equivalents may be derived from any source such as being chemically synthesized or identified via screening processes such as natural product screening. For example chemical or functional equivalents can be designed and/or identified utilizing well known methods such as combinatorial chemistry or high throughput screening of recombinant libraries or following natural product screening.

For example, libraries containing small organic molecules may be screened, wherein organic molecules having a large number of specific parent group substitutions are used. A general synthetic scheme may follow published methods (e.g. Bunin et al. (1994) *Proc. Natl. Acad. Sci. USA*, 91:4708-4712; DeWitt et al. (1993) *Proc. Natl. Acad. Sci. USA*, 90:6909-6913). Briefly, at each successive synthetic step, one of a plurality of different selected substituents is added to each of a selected subset of tubes in an array, with the selection of tube subsets being such as to generate all possible permutation of the different substituents employed in producing the library. One suitable permutation strategy is outlined in U.S. Pat. No. 5,763,263. Another strategy includes fragment based drug design.

There is currently widespread interest in using combinational libraries of random organic molecules to search for biologically active compounds (see for example U.S. Pat. No. 5,763,263). Ligands discovered by screening libraries of this type may be useful in mimicking or blocking natural ligands or interfering with the naturally occurring ligands of a biological target. In the present context, for example, they may be used as a starting point for developing IFNε analogs which exhibit properties such as more potent pharmacological effects. IFNε or a functional part thereof may according to the present invention be used in combination libraries formed by various solid-phase or solution-phase synthetic methods (see for example U.S. Pat. No. 5,763,263 and references cited therein). By use of techniques, such as that disclosed in U.S. Pat. No. 5,753,187, millions of new chemical and/or biological compounds may be routinely screened in less than a few weeks. Of the large number of compounds identified, only those exhibiting appropriate biological activity are further analyzed.

With respect to high throughput library screening methods, oligomeric or small-molecule library compounds capable of interacting specifically with a selected biological agent, such as a biomolecule, a macromolecule complex, or cell, are screened utilizing a combinational library device which is easily chosen by the person of skill in the art from the range of well-known methods, such as those described above. In such a method, each member of the library is screened for its ability to interact specifically with the selected agent. In practicing the method, a biological agent is drawn into compound-containing tubes and allowed to interact with the individual library compound in each tube. The interaction is designed to produce a detectable signal that can be used to monitor the presence of the desired interaction.

Analogs of IFNε contemplated herein include, but are not limited to, modifications to side chains, incorporating unnatural amino acids and/or derivatives during peptide, polypeptide or protein synthesis and the use of crosslinkers and other methods which impose conformational constraints on the analogues. The specific form which such modifications can take will depend on whether the subject molecule is proteinaceous or non-proteinaceous. The nature and/or suitability of a particular modification can be routinely determined by the person of skill in the art.

As indicated above, the present invention extends to a formulation wherein the IFNε is a hybrid between human and murine IFNε. Administration of the formulation comprising IFNε or a functional natural or synthetic variant or hybrid thereof or an inducer of Ifnε expression or IFNε activity alone or in combination with another anti-cancer agent of the present invention may also be referred to as a pharmaceutical composition. Such a formulation may be prepared by any convenient means. The components of the formulation are contemplated to exhibit anti-cancer activity when administered in an amount which depends on the particular case. The amount of IFNε or variant, hybrid or inducer adequate to accomplish anti-cancer activity is defined as a "therapeutically effective dose" or "effective amount". The dosage schedule and amounts effective for this use, i.e., the "dosing regimen", will depend upon a variety of factors, including the stage of the disease or condition, the severity of the disease or condition, the general state of the patient's health, the patient's physical status, age, pharmaceutical formulation and concentration of active agent (e.g. IFNε), and the like. In calculating the dosage regimen for a patient, the mode of administration is also taken into consideration. The dosge regimen must also take into consideration the pharmacokinetics, i.e., the pharmaceutical composition's rate of absorption, bioavailability, metabolism, clearance, and the like. See, e.g. Egleton (1997) *Peptides* 18:1431-1439; Langer (1990) *Science* 249:1527-1533. A broad range of doses may be applicable. Dosage regimes may be adjusted to provide the optimum therapeutic response. For example, several divided doses may be administered daily, weekly, monthly or other suitable time intervals or the dose may be proportionally reduced as indicated by the exigencies of the situation. In an example, an amount of from 10 Ul/dose to 1,000,000 Ul/dose may be administered 1 to 3 times a week per subject. Exemplary dosage regimes include 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 IU/dose, 100, 200, 300, 400, 500, 600, 700, 800, 900, 1000 IU/dose or $10^3$, $10^4$, $10^5$, $10^6$ IU/dose. This may be from 1, 2, 3, 4, 5, 6 or 7 times per week. Doses may also be calculated based on IU/kg body weight of the subject. In an embodiment, dosages are given by any convenient means.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. In addition, active agents may be coupled to ply L lysine or PEGylated.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The formulation may be administered in a convenient manner such as by the oral, intraperitoneal, intravenous, subcutaneous, inhaled, suppository routes or implanting (e.g. using slow release molecules). The formulation may be administered in the form of pharmaceutically acceptable nontoxic salts, such as acid addition salts or metal complexes, e.g. with zinc, iron or the like (which are considered as salts for purposes of this application). Illustrative of such acid addition salts are hydrochloride, hydrobromide, sulfate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

The IFNε or its variant, hybrid or inducer of the present invention can be combined with a pharmaceutically acceptable carrier (excipient) to form a pharmacological composition. Pharmaceutically acceptable carriers can contain a physiologically acceptable compound that acts to, e.g. stabilize, or increase or decrease the absorption or clearance rates of the pharmaceutical compositions of the subject invention. Physiologically acceptable compounds can include, e.g. carbohydrates, such as glucose, sucrose, or dextrans, antioxidants, such as ascorbic acid or glutathione, chelating agents, low molecular weight proteins, compositions that reduce the clearance or hydrolysis of the peptides or polypeptides, or excipients or other stabilizers and/or buffers. Detergents can also used to stabilize or to increase or decrease the absorption of the pharmaceutical composition, including liposomal carriers. Pharmaceutically acceptable carriers and formulations for peptides and polypeptide are known to the skilled artisan and are described in detail in the scientific and patent literature.

As indicated above, the IFNε may also be added as an adjuvant for another anti-cancer agent. In this regard, the "medicament" includes IFNε or a variant or hybrid thereof alone or in combination with another anti-cancer agent.

Solid formulations can be used for enteral (oral) administration. They can be formulated as, e.g. pills, tablets, powders or capsules. For solid compositions, conventional nontoxic solid carriers can be used which include, e.g. pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed. A non-solid formulation can also be used for enteral administration. The carrier can be selected from various oils including those of petroleum, animal, vegetable or synthetic origin, e.g. peanut oil, soybean oil, mineral oil, sesame oil, and the like. Suitable pharmaceutical excipients include e.g. starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, polyethylene glycol, water and ethanol.

The composition of the subject invention, when administered orally, can be protected from digestion. This can be accomplished either by complexing the composition with a composition to render it resistant to acidic and enzymatic hydrolysis or by packaging these molecules in an appropriately resistant carrier such as a liposome. Means of protecting compounds from digestion are well known in the art, see, e.g. Fix (1996) *Pharm Res.* 13:1760-1764; Samanen (1996) *J. Pharm. Pharmacol.* 48:119-135; U.S. Pat. No. 5,391,377, describing lipid compositions for oral delivery of therapeutic agents (liposomal delivery is discussed in further detail, infra).

The composition of the present invention can also be administered in sustained delivery or sustained release mechanisms, which can deliver the formulation internally. For example, biodegradable microspheres or capsules or other biodegradable polymer configurations capable of sustained delivery of a peptide can be included in the formulations of the invention (see, e.g. Putney (1998) *Nat. Biotechnol.* 16:153-157).

For inhalation, the composition of the invention can be delivered using any system known in the art, including dry powder aerosols, liquid delivery systems, air jet nebulizers, propellant systems, and the like. See, e.g. Patton (1998) *Biotechniques* 16:141-143; product and inhalation delivery systems for polypeptide macromolecules by, e.g. Dura Pharmaceuticals (San Diego, Calif.), Aradigm (Hayward, Calif.), Aerogen (Santa Clara, Calif.), Inhale Therapeutic Systems (San Carlos, Calif.), and the like. For example, the IFNε formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, e.g. air jet nebulizers.

The IFNε can also be formulated in pharmaceutically acceptable compositions suitable for pulmonary or respiratory delivery to a patient. Particular formulations include dry powders, liquid solutions or suspensions suitable for nebulization, and propellant formulations suitable for use in metered dose inhalers (MDI's). The preparation of such formulations is well described in the patent, scientific, and medical literatures, and the following descriptions are intended to be exemplary only.

Liquid formulations of IFNε for use in nebulizer systems can include components to enhance or maintain chemical stability, including chelating agents, protease inhibitors, isotonic modifiers, inert gases, and the like.

For use in metered dose inhalers, the IFNε of the present invention is dissolved or suspended in a suitable aerosol propellant, such as a chlorofluorocarbon (CFC) or a hydrofluorocarbon (HFC). Suitable CFC's include trichloromonofluoromethane (propellant 11), dichlorotetrafluoroethane (propellant 114), and dichlorodifluoromethane (propellant 12). Suitable HFC's include tetrafluoroethane (HFC-134a) and heptafluoropropane (HFC-227).

In an embodiment, for incorporation into the aerosol propellant, the IFNε of the present invention is processed into respirable particles as described below for the dry powder formulations. The particles are then suspended in the propellant, typically being coated with a surfactant to enhance their dispersion. Suitable surfactants include oleic acid, sorbitan trioleate, and various long chain diglycerides and phospholipids.

Such aerosol propellant formulations may further include a lower alcohol, such as ethanol (up to 30% by weight) and other additives to maintain or enhance chemical stability and physiological acceptability.

Dry powder formulations typically comprises the IFNε in a dry, usually lyophilized, form with a particular size within a preferred range for deposition within the alveolar region of the lung. Respirable powders of IFNε within the preferred size range can be produced by a variety of conventional techniques, such as jet-milling, spray-drying, solvent precipitation, and the like. Dry powders can then be administered to the patient in conventional dry powder inhalers (DPI's) that use the inspiratory breath through the device to disperse the powder or in air-assisted devices that use an external power source to disperse the powder into an aerosol cloud. In the above description, reference to "IFNε" includes its variants, hybrids and inducers.

In preparing pharmaceutical formulations of the present invention, a variety of modifications can be used and manipulated to alter pharmacokinetics and biodistribution. A number of methods for altering pharmacokinetics and biodistribution are known to one of ordinary skill in the art.

In an embodiment, induction of the expression of Ifnε is achieved by directly effecting expression of Ifnε. This can be achieved by the introduction directly to cancer cells in a solid tumor of a construct with the gene comprising Ifnε which will allow for induction of the levels of IFNε or an active variant thereof upon expression or even de novo expression and thereby effect the biological functions for which it is directed. Hence, recombinant cellular or viral means may be employed to generate IFNε or its variant, hybrid or inducer at or near or within cancer cells.

The present invention further contemplates a combination of methods in the treatment of cancer. For example, IFNε treatment or treatment by a variant or hybrid or inducer of IFNε may be used in combination with surgical or chemical ablation of a cancer or cancer-affected organ or tissue.

EXAMPLES

Aspects disclosed herein are further described by the following non-limiting Examples.
Methods
Cell Line and Cell Culture
Ovarian cancer line ID8 (murine; Roby et al. (2000) *Carcinogenesis* 21(4):585-591), was used for in vitro assays. The ID8 cell line was cultured in RPMI 1640 (GibcoBRL, Ontario, Canada) supplemented with 4% v/v heat-activated fetal calf serum (FCS; GibcoBRL). All cells were cultured at 37° C. in an atmosphere of 5% v/v carbon dioxide ($CO_2$). Cells were Mycoplasma negative according to MycoAlert (Trade Mark) PLUS Mycoplasma Detection Kit (ratio <1; Lonza, Basel).
Cell Stimulation for Gene Expression Studies Cell lines were plated ($1.5 \times 10^5$ cells/well) in a 12 well plate 24 hour prior to stimulation with recombinant IFN or IFN (described below) at 0-1000 IU/ml with resuspension buffer (described below) or PBS as vehicle controls. Cells were then incubated at 37° C. for 3 hrs prior to mRNA extraction.
mRNA Extraction and Purification RNA was extracted using a QIAGEN RNeasy mini-kit (Invitrogen, USA) as per the manufacturer's protocol (see appendix B for detailed protocol). Cells were harvested in betamercaptoethanol/RLT (10 1—ME per 1 ml of RLT buffer) and using a 1 mL syringe and a 23-gauge needle, each sample was syringed up and down ten times to homogenize the cells. RNA was on-column DNase treated using the QIAGEN RNase-free DNase Set (Invitrogen, USA) according to manufacturer's instructions. RNA yield and quality was then assessed using a NanoDrop (Registered Trade Mark) ND-1000 spectrophotometer (acceptable ranges for RNA purity 260/280 ratio ~2.0 and 260/230 ratio between 2.0-2.2) and stored at −80° C.
cDNA Synthesis A total of 500 ng of RNA was made up to 7 1 with diethylpyrocarbonate (DEPC) treated Milli-Q $H_2O$. RNA was then reverse-transcribed into cDNA using M-MLV reverse transcriptase (Promega, USA), according to manufacturer's instructions. cDNA samples were stored at −20° C. until use
GAPDH Polymerase Chain Reaction PCR)

A GAPDH PCR was performed on samples from cDNA synthesis in the presence or absence of reverse transcriptase enzyme (+/−RT). The absence of product generated by GAPDH PCR for negative RT samples ruled out the presence of genomic DNA contamination. An aliquot of 1 1 of cDNA was added to 5×green GoTaq buffer, magnesium chloride, forward and reverse GAPDH primers, 10 mM dNTPs, GoTaq enzyme (Promega, USA) and a total volume of 25 1 was made up with DEPC treated $H_2O$.

All PCR reactions were carried out in a MyCycler (Trade Mark) Thermal Cycler (BIO-RAD) using the following cycle reaction conditions:

| | |
|---|---|
| Denaturation: 94° C., 2 mins | 1 cycle |
| Denaturation: 94° C., 30 secs | |
| Annealing: 55° C., 30 secs | 35 cycles |
| Extension: 72° C., 30 secs | |
| Extension: 72° C., 7 mins | 1 cycle |

Each PCR product was then loaded onto a 1.5% w/v agarose gel and run at 100V for 30 minutes.
Quantitative Real Time PCR (qRT-PCR)

Primers were designed to be intron-spanning where possible. This ensures that cDNA band would be distinguished from genomic DNA on the basis of size. Primers were designed using Primer Express (Registered Trade Mark) v3.0 software (Applied Biosystems, USA). Each reaction was performed in a total of 10 1 comprising 2 1 of cDNA, 5 1 Sybr Green PCR Master Mix (Applied Biosystems, USA), 0.2 1 of each 10 mM stocks of relevant forward and reverse primers and DEPC $H_2O$. All gene amplifications were normalized to the expression of 18S, an internal control gene stably expressed in cells. Samples were loaded in triplicate onto a MicroAmp (Trade Mark) Optical 384-well reaction plate and sealed with MicroAmp (Trade Mark) Optical adhesive film. Additionally, two RT negative reactions were used as well as a no transcript control where DEPC treated $H_2O$ was used to replace cDNA. Amplification of a single PCR product was confirmed by analyzing dissociations curves and visualization on agarose gels. A list of primers sequences is provided in Table 2.

TABLE 2

Summary of sequence identifiers

GAPDH primers

| | |
|---|---|
| 5' GAPDH primer | 5'-GAACGGGAAGCTTGTCATCAA-3' (SEQ ID NO: 1) |
| 3' GAPDH primer | 3'-CTAAGCAGTTGGTGGTGCAG-5' (SEQ ID NO: 2) | qRT-PCR SYBR primers

| | |
|---|---|
| 5' 18S primer | 5'-GTAACCCGTTGAACCCCATT-3' (SEQ ID NO: 3) |
| 3' 18S primer | 3'-CCATCCAATCGGTAGTAGCG-5' (SEQ ID NO: 4) |

Mouse

| | |
|---|---|
| 5' Isg15 primer | 5'-TGAGAGCAAGCAGCCAGAAG-3' (SEQ ID NO: 5) |
| 3' Isg15 primer | 3'-ACGGACACCAGGAAATCGTT-5' (SEQ ID NO: 6) |
| 5' Tap1 primer | 5'-CGCAACATATGGCTCATGTC-3' (SEQ ID NO: 7) |
| 3' Tap1 primer | 3'-GCCCGAAACACCTCTCTGT-5' (SEQ ID NO: 8) |
| 5' Cdc20 primer | 5'-GTCACTCCGCTCGAGTAAGC-3' (SEQ ID NO: 9) |
| 3' Cdc20 primer | 3'-GCCCACATACTTCCTGGCTA-5' (SEQ ID NO: 10) |
| 5' Ccne1 primer | 5'-CCTCCAAAGTTGCACCAGTT-3' (SEQ ID NO: 11) |
| 3' Ccne1 primer | 3'-AGAGGGCTTAGACGCCACTT-5' (SEQ ID NO: 12) |
| 5' Cxcl10 primer | 5'-CTGAATCCGGAATCTAAGACCA-3' (SEQ ID NO: 13) |
| 3' Cxcl10 primer | 3'-GAGGCTCTCTGCTGTCCATC-5' (SEQ ID NO: 14) |
| 5' Ifit1 primer | 5'-TCAAGGCAGGTTTCTGAGGA-3' (SEQ ID NO: 15) |
| 3' Ifit1 primer | 3'-ACCTGGTCACCATCAGCATT-5' (SEQ ID NO: 16) |
| 5' Casp1 primer | 5'-ACGCCATGGCTGACAAGATCCTG-3' (SEQ ID NO: 17) |
| 3' Casp1 primer | 3'-GGTCCCGTGCCTTGTCCATAGC-5' (SEQ ID NO: 18) |
| 5' Ifnε primer | 5'-GAAACGGATTCCCTTCCAAT-3' (SEQ ID NO: 19) |
| 3' Ifnε primer | 3'-ACTGCTGGACTGACGAGCTT-5' (SEQ ID NO: 20) |

Human

| | |
|---|---|
| 5' ISG15 primer | 5'-GCGAACTCATCTTTGCCAGT-3' (SEQ ID NO: 21) |
| 3' ISG15 primer | 3'-AGCATCTTCACCGTCAGGTC-5' (SEQ ID NO: 22) |
| 5' IFIT1 primer | 5'-AGCTTACACCATTGGCTGCT-3' (SEQ ID NO: 23) |
| 3' IFIT1 primer | 3'-CCATTTGTACTCATGGTTGCTGT-5' (SEQ ID NO: 24) |
| 5' IFNε primer | 5'-AGGACACACTCTGGCCATTC-3' (SEQ ID NO: 25) |
| 3' IFNε primer | 3'-CTCCCAACCATCCAGAGAAA-5' (SEQ ID NO: 26) |

IFNε Nucleotide and Amino Acid Sequences
Human nucleotide (SEQ ID NO:27)
Human amino acid (SEQ ID NO:28)
Murine nucleotide (SEQ ID NO:29)
Murine nucleotide (optimized) [SEQ ID NO:30]
Murine nucleotide (SEQ ID NO:31)
Murine amino acid (SEQ ID NO:32)
Amino acid residues 22-27 of rmIFNε (SEQ ID NO:33)

All reactions were processed using a 7900HT Fast Real Time PCR machine (Applied Biosystems, USA) using the following thermal cycling protocol: 50° C. for 2 minutes, 95° C. for 10 minutes followed by 40 cycles of 95° C. for 15 seconds and 60° C. for 1 minute. Cycle threshold (Ct) values for all probes were exported and data analysis was carried out using the 2-CT method. For figures, gene amplifications were normalized to the expression of 18 S, an internal control gene stably expressed in cells. Then values of fold-change after IFN treatment, were expressed relative to value for untreated samples (which was 1).

Cellular Growth Assays

Cellular proliferation was measured using the xCELLigence system (ACEA Biosciences, Inc., San Diego, Calif., USA) for real-time cell analysis (RTCA). Fifty microliters of cell culture medium was added to each well in a 96 well E-plate (ACEA Biosciences, Inc.) for the impedance background measurement. Cells were then added (ID8—$6\times10^3$ cells/well, CAOV3 and OVCAR4—$1\times10^5$ cells/well) to a volume of 100 L in serum-free culture media and allowed to adhere overnight. Recombinant IFN or vehicle was added to the cells up to a final volume of 200 L of normal culture media. The E-Plates were incubated at 37° C. with 5% v/v $CO_2$ and impedance measured on the RTCA system at 15-minute time intervals for up to 72 hours with or without treatment. For data analysis, the baseline cell index (CI) is determined by subtracting the CI for a cell-containing well from the CI of a well with only culture media. To facilitate the statistical evaluation of the results, impedance measurements from each well were normalized to the time of stimulation with IFN, termed 'normalized cell index'. Three independent experiments were performed in technical quadruplicate and analyzed for doubling-time and slope (1/hr) of growth curves, indicative of rate of proliferation, using RCTA software. Data was analyzed using 2-way ANOVA with Sidak's multiple comparisons test, **$p<0.0001$, *$p<0.001$.

Migration Assays

For single cell tracking, ID8 cells were plated in serum free media at $2.5\times10^4$ cells/well in a 48 well plate and left to adhere overnight. For scratch assays, ID8 cells were plated in a 48 well plate and allowed to reach confluence. Coated wells were scratched using a P10 filter tip (Axygen Scientific, California). Cells were stained using CellTrace (Trade Mark) CFSE Cell Proliferation Kit (ThermoFischer Scientific, Massachusetts) as per the manufacturer's instructions, then washed in PBS and treated with recombinant IFN. Fluorescent images were captured every 30 minutes for 12 hours using a confocal microscope and analyzed using Imaris software. For single cell tracking, individual cells were tracked via fluorescence to measure the overall distance traveled by each cell (track length) and direct displacement length from the initial to final position of each cell (track displacement) over 12 hours. Significance was determined by Student's T test comparing the mean distances traveled $2.5\times10^4$ cells plated in technical triplicate. For scratch assays, cellular migration was measured as the percentage surface area closure of the scratch (empty space) over 12 hours. Significance was determined by one-way ANOVA with Tukey's multiple comparisons; *$p<0.05$, $p<0.01$, *$p<0.001$, ****$p<0.0001$.

Apoptosis Assays

ID8 cells were plated in a 12 well plate ($3.5\times10^4$ cells/well) in 2 ml and left to adhere overnight. Cells were stimulated with recombinant murine Ifn or vehicle control for 48 hours. Hydrogen peroxide ($H_2O_2$) was used a positive control for induction of apoptosis at 1-5 mM. Following stimulation, cells were trypsinized and washed in PBS. Single cell suspensions were stained with FITC conjugated Annexin V and propidium iodide (PI) using the FITC Annexin V Apoptosis Detection kit II (BD Biosciences, New Jersey), as per the manufacturer's instructions and analyzed by flow cytometry using a FACSCanto (Trade Mark) II flow cytometer (BD Biosciences) and Flo-Jo software. The different phases of apoptosis were defined as i) live cells (FITC Annexin V−/PI−), ii) early apoptotic (FITC Annexin V+/PI−), iii) late apoptotic (FITC AnnexinV+/PI+), and iv) necrotic cells (FITC Annexin V−/PI+).

Immunohistochemistry

Human fallopian tubes, mouse organs and tumor samples were fixed for 24 hours in 10% v/v neutral buffered formalin, then washed in 70% v/v ethanol, and embedded in paraffin. Tissue was sectioned at 4-m thickness and stained for H&E, smooth muscle actin (SMa), cytokeratin 18(Ck18) and IFN. Briefly, histological tissue sections were deparaffinized and rehydrated. Antigen retrieval was performed by heat in 10 mM Tris/1 mM EDTA (pH 9.0) for 6 mins. After inhibition of endogenous peroxidase activity with 3% v/v hydrogen peroxide, tissues were blocked in CAS-Block [Trade Mark] (ThermoFisher Scientific) for 1 hour. Tissues were then incubated overnight at 4° C. with anti-IFNε (1:200; Novus Biologicals, Colorado), anti-SMa (1:100; Dako Omnis, Santa Clara), anti-Ck18 (1:50; Dako Omnis) and rabbit IgG (1:200; Vector Laboratories, California) or mouse IgG1 (1:37; Vector Laboratories) as isotype controls. Biotinylated anti-rabbit or anti-mouse IgGs (both 1:250 dilution; Vector Laboratories) were diluted in the same buffer and incubated for 1 hour. Slides were then washed in 0.05% v/v Tween/PBS and incubated with avidin and biotinylated horseradish peroxidase (VECTASTAIN (Registered Trade Mark) Elite (Registered Trade Mark) ABC Kit, Vector Laboratories) as per the manufacturer's instructions and washed again. Slides were then incubated with diaminobenzidine tetrahydrochloride (DAB; DAB+ Substrate Chromogen System, Dako Omnis) as per the manufacturer's instructions. Sections were counterstained with Haematoxylin for 45 seconds then dehydrated and placed under coverslip with dibutylphthalate dolystyrene xylene (DPX; Merck, Germany). Staining intensity was calculated using the positive pixel analysis tool in Imagescope software and significance was determined using Mann-Whitney tests, $p<0.01$, **$p<0.0001$.

Immunophenotyping

Single cell suspensions were obtained from peritoneal lavage cells of C57BL/J mice studied for surface antigen expression using a panel of monoclonal antibodies directly conjugated with fluorochromes. In order to prevent non-specific binding, cell surface receptors were blocked with Anti-mouse CD16/CD32 Fcγ III/II Receptor blocking antibody (BD PharMingen, California). For surface staining, cells were stained with the various combinations of fluorochrome-labeled antibodies: panel 1—APC conjugated CD45, APC-Cy7 conjugated CD8, FITC conjugated NK-1.1, PE conjugated CD69, Pacific Blue conjugated CD4; panel 2—APC conjugated CD25, APC-Cy7 conjugated CD8, FITC conjugated CD45, PE conjugated Pan CK, PE-Cy7 conjugated CD4 and Pacific Blue conjugated FoxP3; panel 3—APC conjugated CD45, APC-Cy7 conjugated CD11b, FITC conjugated Ly6C, PE conjugated I-Ab, PE-Cy7 conjugated CD11c and Pacific Blue Ly6G. Cells were analyzed using a FACSCanto (Trade Mark) II flow cytometer (BD Biosciences) and Flo-Jo software.

Cytometric Bead Array (CBA)

Cytometric bead array (BD CBA Mouse Inflammation Kit; BD Pharmingen) was used to determine cytokine levels in the supernatant of peritoneal exudate cells from mice injected with ID8 cells (see intraperitoneal model of ovarian cancer below) as per the manufacturer's instructions. Flow cytometry was used to detect PE-conjugated detection antibodies forming sandwich complexes with capture beads for IL-8, IL-1, IL-6, IL-10, IL-12p70, or TNF-. PE fluorescent intensities for each sandwich complex was acquired using a FACSCanto (Trade Mark) II flow cytometer (BD Biosciences) and Flo-Jo software.

Mice

The Ifn$^{-/-}$ mice (Fung et al. (2013) supra) on a C57b1/6 background and wild-type mice (Monash Animal Research Facility, Monash University, Clayton, Australia) were housed in standard specific pathogen free (SPF) conditions.

Intrabursal (Orthotopic) Ovarian Cancer Model

Female (10 weeks of age) C57BL/6 wild-type (Ifn$^{+/+}$) and Ifn deficient mice (Ifn$^{-/-}$) were used in these experiments. Mice were anaesthetized by inhalation of isoflurane (5% in oxygen) in an induction chamber, and anesthesia maintained at 2.5-3.0% isoflurane delivered via nosecone during all procedures. Mice were subcutaneously injected with Carprofen (5 mg/kg) prior to surgery. A small incision was made at the dorso-medial position directly above the ovarian fat pad, with a secondary small incision through the peritoneal wall. The ovarian fat pad was externalized and stabilized with a bull clip, and a dissecting microscope used to locate the oviduct in the exposed ovary. ID8 cells ($1\times10^6$) were injected underneath the left ovarian bursa. The peritoneal wall was sutured closed using 6/0 suture prior to topical Bupivacaine administration and closure of the incision closed with surgical staples. Analgesia (Carprofen 5 mg/kg body weight) was provided in drinking water for 3 days thereafter. Mice were monitored for body weight, Body Condition Score (BCS) defined as: BCS 1 Thin—Skeletal structure prominent and vertebral bodies protruding, BCS 2 Under-conditioned—segmentation of vertebral column evident but not protruding, and BCS3 Well-conditioned—vertebrae not evident without palpation, as well as clinical signs and culled 13 weeks post-ID8 injection. At autopsy, the overall spread and tumor burden of each mouse was documented (number of tumor nodules, sites of nodule deposits recorded and photographed), ascites fluid was drained from the peritoneum for volume measurement and cell counts and tissue harvested (spleen, diaphragm, peritoneal wall, mesenteric fat, female reproductive tract) for weight measurements and immunohistochemical analysis.

Intraperitoneal (Disseminated) Ovarian Cancer Model

Female (6 to 8 weeks of age) C57BL/6 wild-type (Ifn$^{+/+}$) mice were used in these experiments. Mice were injected intraperitoneally with 5×10$^6$ ID8 cells using a 30-gauge needle. Mice were monitored for body weight, BCS and clinical signs and culled 8 weeks post-ID8 injection. At autopsy, the overall spread and tumor burden of each mouse was documented (number of tumor nodules, sites of nodule deposits recorded and photographed), ascites fluid was drained from the peritoneum for volume measurement and cell counts and tissue harvested (spleen, diaphragm, peritoneal wall, mesenteric fat, female reproductive tract) for weight measurements and immunohistochemical analysis.

Intraperitoneal Recombinant IFN Therapy

IFN treatments were commenced 3 days post-intraperitoneal ID8 cell injections. Mice either received recombinant murine Ifn injected intraperitoneally 3 times a week at a dose of 2-500 IU/injection or Ifnβ at 500 IU/injection or vehicle for 8 weeks. At autopsy, the orthotropic 'primary" tumor was collected along with metastases (diaphragmatic and peritoneal), spleen, ascites fluid (volume and cell counts) and peritoneal lavage and samples weighed, photographed and processed for immunohistochemical analysis.

Recombinant IFN Production

Mouse

Production and Purification of muIFNε

The generation and PCR screening of recombinant bacmids containing the IFN gene and baculovirus was carried out as described elsewhere. Briefly, PCR-positive colonies were expanded and recombinant bacmid isolated using an EndoFree Maxi-Prep kit according to the manufacturer's instructions (Qiagen). Recombinant baculovirus was generated by transfection of the purified bacmid into Sf9 insect cells and high titre baculovirus generated. IFN was expressed as a soluble protein and secreted into the culture media.

Insect cell expression supernatants were clarified of cells by centrifugation as described, supplemented with phenylmethanesulfonyl fluoride (PMSF) at a final concentration of 1 mM before dialysis against TBS (10 mM Tris-HCl, 150 mM NaCl, pH8.0) overnight at 4° C. using 12.5 kDa cut-off dialysis tubing (Sigma-Aldrich). Particulates were removed by filtration of the dialysate through a 0.8 m syringe driven filter (Sartorius). An anti-IFN monoclonal antibody affinity column was prepared by coupling 10 mg of anti-IFN antibody to 1 ml of AminoLink Plus resin according to the manufacturer's instructions (Thermo Scientific). The filtrate was applied to this column and then the column washed with five column volumes (CV) of TBS to remove non-specifically bound proteins and rIFN eluted with 0.1M Glycine pH3.0 in 0.5CV fractions. Collected fractions were immediately neutralized with 1/10$^{th}$ CV of 1M Tris-HCl pH8.0 and buffer exchanged by addition of 10× TBS (100 mM Tris-HCl, 1.5M NaCl, pH8.0). Protein containing fractions, as determined by absorbance at 280 nm, were further supplemented with 10% v/v glycerol. Purified IFN was subsequently further purified by gel filtration on a S75 10/30 size exclusion column (GE Healthcare) connected to an AKTA PrimePlus (GE Healthcare) using TBS pH8.0 containing 10% v/v glycerol. Purified fractions were filter sterilized and stored at 4° C. or snap-frozen in liquid nitrogen for long-term storage at −80° C.

Human

Production of huIFNε Using Bacterial System

Human IFN (tagless native 187 residue sequence) was expressed from a pET-28a expression vector (Novagen) in Escherichia coli BL21 (DE3). A single colony of the freshly transformed cells was inoculated into L-Broth containing 50 μg/mL kanamycin. The culture was grown overnight at 37° C. with constant shaking at 250 rpm. After 16 h, the cell culture was diluted 50-fold with fresh L-Broth containing 50 μg/mL kanamycin. The mixture was incubated with shaking at 37° C. until the optical density (OD$_{600}$) reached 0.6-0.8 when the cells were induced with 1 mM isopropyl-D-1-thiogalactopyranoside (IPTG). The cells were allowed to grow for 3 h before harvesting by centrifugation at 5000 g for 15 mins. The cell pellets were frozen at −20° C. until further use.

Murine and human IFNε production may be enhanced by optimized codon expression. Examples are shown in SEQ ID NOs:28 through 32. Codon optimization may also be used to substitute, add or delete amino acids to enhance IFNε activity and/or stability such as serum half life.

Preparation of Inclusion Bodies

Frozen cells were thawed at room temperature for 30 mins. Each gram of cell pellet was resuspended with 10 mL of BugBuster Master Mix (Merck Millipore) with added 10 mM dithiothreitol (DTT), 5 mM ethylenediaminetetraacetic acid (EDTA) and 0.5% w/v complete Mini protease inhibitor cocktail tablet (Roche), and incubated at room temperature for 2 h with gentle agitation. The lysate was centrifuged at 30000 g for 20 mins, and the supernatant was decanted. The inclusion bodies (IBs) were then washed multiple times using different buffers (70 mL for each gram of IBs) all containing 10 mM DTT and 5 mM EDTA: (1) 1:10 diluted BμgBuster Master Mix (with MilliQ water), (2) 10 mM tris(hydroxymethyl)aminomethane (Tris) buffer pH 8.0 with 150 mM NaCl and 2 M urea, (3) 10 mM Tris buffer pH 8.0 with 150 mM NaCl and 5% v/v Triton X-100. Each wash was followed by centrifugation of 30000 g for 20 mins to remove the supernatant. Thereafter, the IBs were washed twice with 10 mM Tris pH 8.0 with 150 mM NaCl (70 mL for each gram of IB) to remove EDTA in the product. The IBs were then solubilized using buffer containing 6 M guanidine hydrochloride (Gdn-HCl) pH 7.4, 100 mM Na$_2$HPO$_4$ and 10 mM Tris overnight at cold room under constant agitation. The resulting mixture was centrifuged at 30000 g for 20 mins, and the solution was 0.2 μm-filtered.

Refolding of huIFNε

DTT was added into the denatured huIFN solution at concentration of 5 mM, and the mixture was incubated at room temperature (25° C.) under mild agitation for 2 h. Thereafter, the mixture was chilled to 4° C. before it was added dropwise into 50 volumes of refold buffer (20 mM phosphate buffer pH 7.4, 150 mM NaCl, 0.8 M L-Arginine (L-Arg) and 10 μM CuSO$_4$) at 4° C. with gentle stirring, and the refolding was allowed to proceed for 16 h.

Protein Purification

EDTA was added into the refold mixture at 5 mM concentration, and the pH of the refold solution was adjusted to pH 6.0 before it was concentrated using both Vivaspin 200 tangential flow filter (MWCO 10 kDa) and Vivaspin 20 concentrator (MWCO 10 kDa) at 4° C. The sample was then purified using gel filtration (HiLoad 16/60 Superdex 200) at flow rate of 1.0 mL/min with 20 mM phosphate buffer pH 6.0 containing 150 mM NaCl and 0.8 M L-Arg as running buffer. Fractions containing huIFN were combined and 1 mL of anion-exchange resin (Q Sepharose fast flow) was added into it. The mixture was incubated at 4° C. under constant agitation for 18 h. The flow through was then collected and concentrated using Vivaspin 20 concentrator.

Gel Electrophoresis and Western Blot

Sodium dodecyl sulfate polyacrylamide gel electrophoresis (SDS-PAGE) and western blot were performed using Bolt Bis-Tris plus 4-12% gradient gel (Life Technologies) and Bolt MOPS SDS running buffer (Life Technologies) at 165 V for 50 mins. For SDS-PAGE analysis, the gel was stained with Coomassie Blue solution (0.25% w/v Coomassie Blue R-250, 50% v/v methanol and 10% v/v acetic acid) for 2 h before destained with solution containing 40% v/v ethanol and 10% v/v acetic acid. For western blot, protein bands were transferred to Immobilon-FL Polyvinylidene Difluoride (PVDF) membrane using Bolt transfer buffer (Life Technologies) at 30 V for 45 mins. The membrane was incubated in Odyssey blocking buffer (PBS) [LI-COR Biosciences] at room temperature for 1 h. The buffer was decanted and rabbit polyclonal anti-huIFN antibody (Novus Biological) at 1:500 dilution was added onto the membrane and incubated for 16 h at 4° C. Thereafter, the antibody solution was removed and the membrane was washed three times with phosphate-buffered saline (PBS) pH 7.4 containing 0.1% v/v Tween 20. Anti-rabbit IgG (H&L) (GOAT) antibody IR dye 800 conjugated (Rockland) at 1:1000 dilution was added onto the membrane and incubated at room temperature for 1 h. The membrane was washed as before with PBS pH 7.4 containing 0.1% v/v Tween 20. Western blot analysis was performed using Odyssey infrared imaging system (LI-COR Biosciences) using both 700 and 800 channels.

Endotoxin Testing

Endotoxin levels in a sample were tested using limulus amebocyte lysate (LAL) test. The testing system and reagents were purchased from Charles River. Protein sample was first diluted 1:10 with LAL reagent water, and then further diluted 1:10 with Endotoxin-specific buffer. Sample was then loaded onto the LAL cartridge (sensitivity 0.05 to 5 EU/mL for neat sample) and the absorbance was recorded using Endosafe-PTS.

Circular Dichrosim

Human IFN sample was prepared in 20 mM phosphate buffer pH 6.0 containing 500 mM NaCl, 5 mM EDTA and 10% v/v glycerol. Circular Dichroism (CD) experiments were performed at 25° C. on a Jasco J-810 spectrometer equipped with a Peltier temperature-controlled water circulator. Spectra ranging from 190 to 250 nm was measured using 1 mm path length quartz cell, accumulation cycle of 3 runs, 1 nm bandwidth, 0.1 nm data pitch and 1 s data integration time. The data were analyzed using Jasco Spectra Manager.

Biological activity (IU/ml) of the huIFN sample was determined by comparison against a serial dilution of hIFN protein of known activity.

Specific activity (IU/mg) of the refolded huIFN using this system is consistent with results obtained from an anti-viral protection assay (protection of WISH cells from infection with EMCV) and confirms: this refolded protein is biologically active; and the specific activity of huIFN is of a similar order of magnitude to that of muIFN expressed in an insect cell expression system (Table 3).

TABLE 3

Comparison of specific activity (IU/mg) of mouse and human interferon epsilon proteins as determined by either viral-protection assay or reporter cell line

| Interferon | Method | Specific Activity (IU/mg) |
|---|---|---|
| muIFN | Anti-viral protection assay (L929 cells and SFV) | $2.1 \times 10^5$ |
| huIFN | Anti-viral protection assay (WISH cells and EMCV) | $1.12 \times 10^4$ |
| huIFN | Reporter cell line (HEK-Blue [Trade Mark]) | $5.26 \times 10^4$ |

Use of this reporter cell line has provided an easy and economical assay for the determination of the biological activity of huIFN and should simplify identification of monoclonal antibodies capable of neutralizing this activity.

The final IFN formulation was in the following buffer that was used as the "vehicle control" in the in vivo and in vitro experiments: 20 mM phosphate buffer pH 6.0 containing 150 mM NaCl and 0.8 M L-Arg as running buffer.

Example 1

The Role of IFNε in Ovarian Cancer

The effects of treating both mouse and human tumor derived cell lines with recombinant IFNε was assessed and compared the effects with other, conventional type I IFNs.

The mouse cell lines examined were the murine ovarian epithelial cell line, ID8s, which are used for in vivo experiments (Example 2) to enable the comparison of in vitro with in vivo anti-tumor effects.

Also examined are the effects of IFNε on various human ovarian cancer cell lines. A number of human cell lines were used to investigate ovarian cancer in vitro, including OVCAR4 and CAOV3 cells. These represent cell lines that are classified as representative of high grade serous ovarian cancer (HGSC) as per systematic genomic comparison with tumor samples to be highly genetically similar to human HGSC (Domcke et al. (2013) *Nature Communications* 4:2126). Each of the cell lines used demonstrated the fundamental molecular characteristics of HGSC including a high fraction of genomic alterations, universal TP53 mutations and few, if any, other somatic mutations in protein-coding regions, and thus, represent some of the most suitable models for studying human ovarian cancer in vitro.

Example 2

IFNε Induces Anti-Tumor Effects the Murine Ovarian Cancer ID8 Cell Line

The aim was to use the ID8 cell line to characterize the anti-tumor effects of IFNε in vivo in a murine model of ovarian cancer. Initially, it was important to confirm that this cell could indeed respond to type I IFNs, including IFNε. ID8 cells were stimulated in vitro with different doses of either recombinant murine IFNε or IFNβ for 3 h before quantification of three well characterized IFN regulated genes (IRGs), cxcl10, isg15 and ifit1 (FIG. 1). IFNε significantly induced expression of all three IRGs in a dose dependent manner, similar to IFNβ (in IU/ml), thus confirming that these cells can respond to IFNε.

Figure 2:
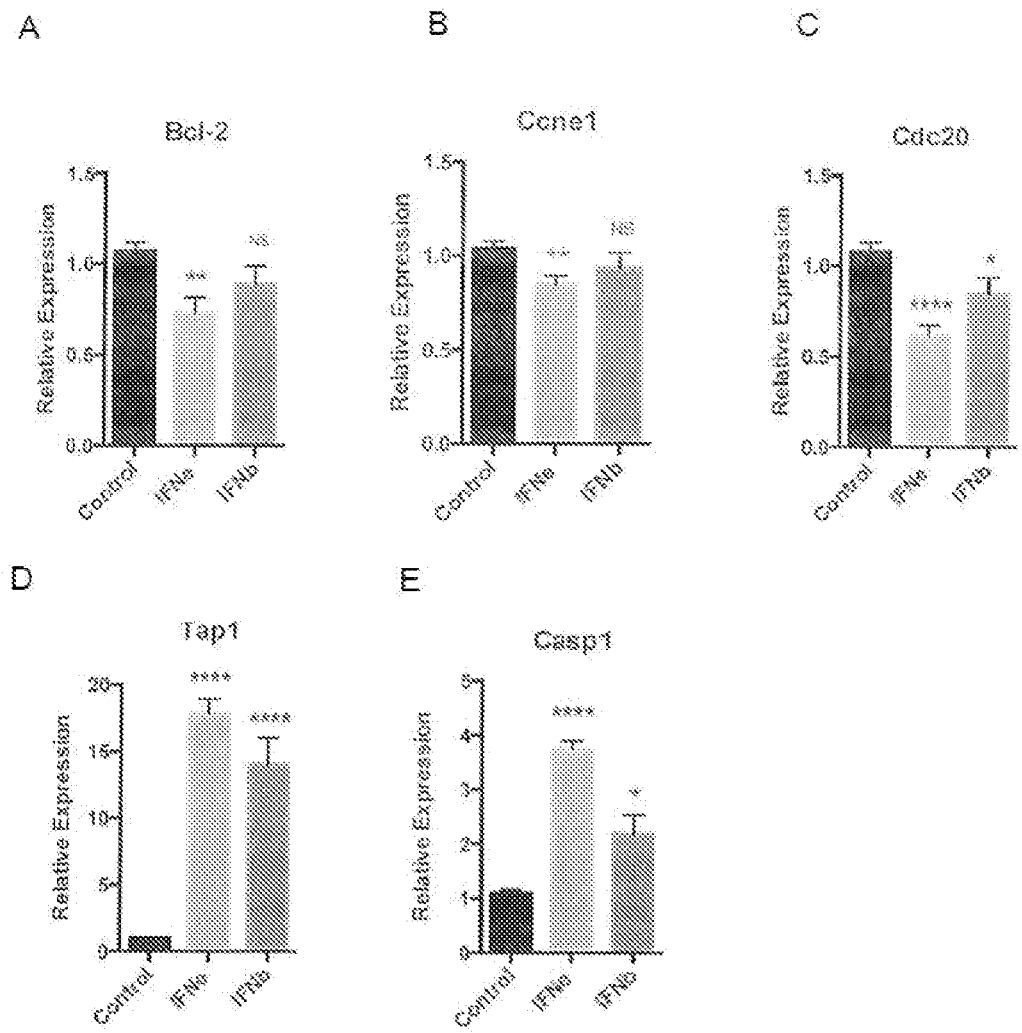
FIGS. 2A through E are graphical representations showing regulation of genes involved in cancer-related biological functions. Graph shows expression of Bcl-2 (A), Ccne1 (B), Cdc20 (C), Tap1 (D) and Casp1 (E) in response to stimulation with 1000 IU/ml of IFNε (middle bar) or IFNβ (right bar) for 3 hours. Data are shown as mean+/−SEM of n=3 independent experiments, each done in technical triplicates. Significance was determined by Student's T test *p<0.05, p<0.01, *p<0.001, ****p<0.0001.

Having confirmed that ID8 cells can respond to IFNε, next investigated was whether IFNε could regulate the expression of IRGs-encoding proteins with roles in tumor-related properties, cell proliferation and apoptosis. It was found that treatment of ID8 cells with 1000 IU/ml of IFNε significantly down-regulated the expression of bcl-2, ccne1 and cdc20, which encode for proteins with anti-apoptotic (bcl-2) and pro-proliferative functions (ccne1, cdc20) (FIG. 2). Conversely, IFNε significantly induced expression of the IRGs tap1 and casp1, genes which encode for pro-apoptotic proteins. Therefore, these data indicate that IFNε regulated genes are involved in cell cycle, proliferation and apoptosis.

Figure 3:
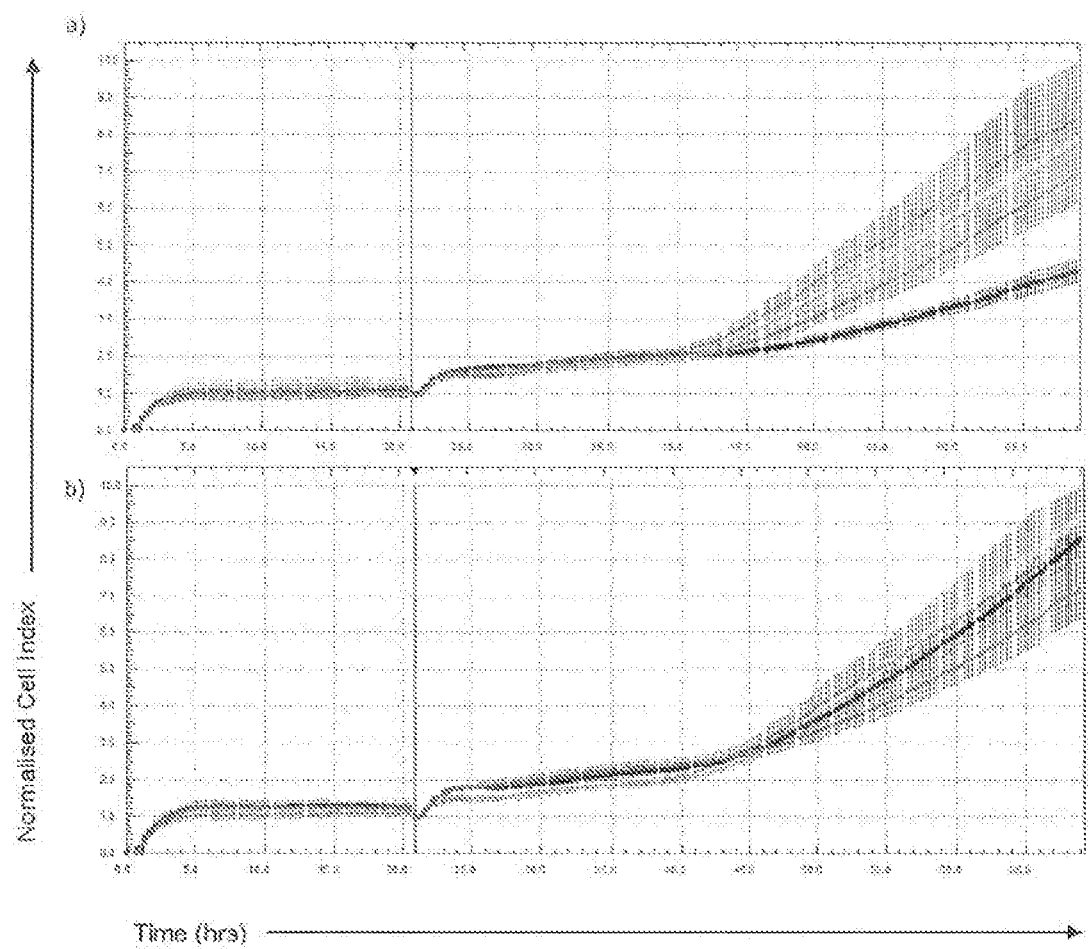
FIGS. 3A and B are graphical representations showing the mean cell index measurements, a correlate of cell number, at 30 min intervals over the 72 h of treatment of ID8 cells with interferon; showing inhibition of ID8 cell proliferation by IFNε (A) but not IFNβ (B). Graphs show inhibition of proliferation of ID8 cells treated with 100-1000 IU/ml of: a) IFNε; b) IFNβ for 48 hours. Cell proliferation is measured by xCELLigence. Graphs show the mean cell index across each well+/−SD. Each cell index is normalized after 24 hours (arrow) of cells plated in serum free media and compared to untreated and buffer-treated controls. Representative of n=3 independent experiments each done in technical triplicate. Legend (a)—untreated (red), control (green), 100 IU/ml IFNε (pink) and 1000 IU/ml IFNε (blue); (b) untreated (red), control (green), 100 IU/ml IFNβ (blue) and 1000 IU/ml IFNβ (pink).

Next assessed was the effect of IFNε on proliferation of ID8 cells using the Xcelligence (Registered Trade Mark) Real Time Cell Analysis (RTCA) system (Acea Biosciences), which allows real-time, label-free monitoring of cell proliferation. Therefore, it was possible to monitor proliferation of ID8 cells treated with IFNε based on an impedance reading of cells in the wells every 30 mins. As cells proliferate, the impedance reading (cell index) increases. As evident in FIG. 2, there is a dose-dependent difference in cell index upon treatment with IFNε (FIG. 3A) or IFNβ (FIG. 3B).

Figure 4:
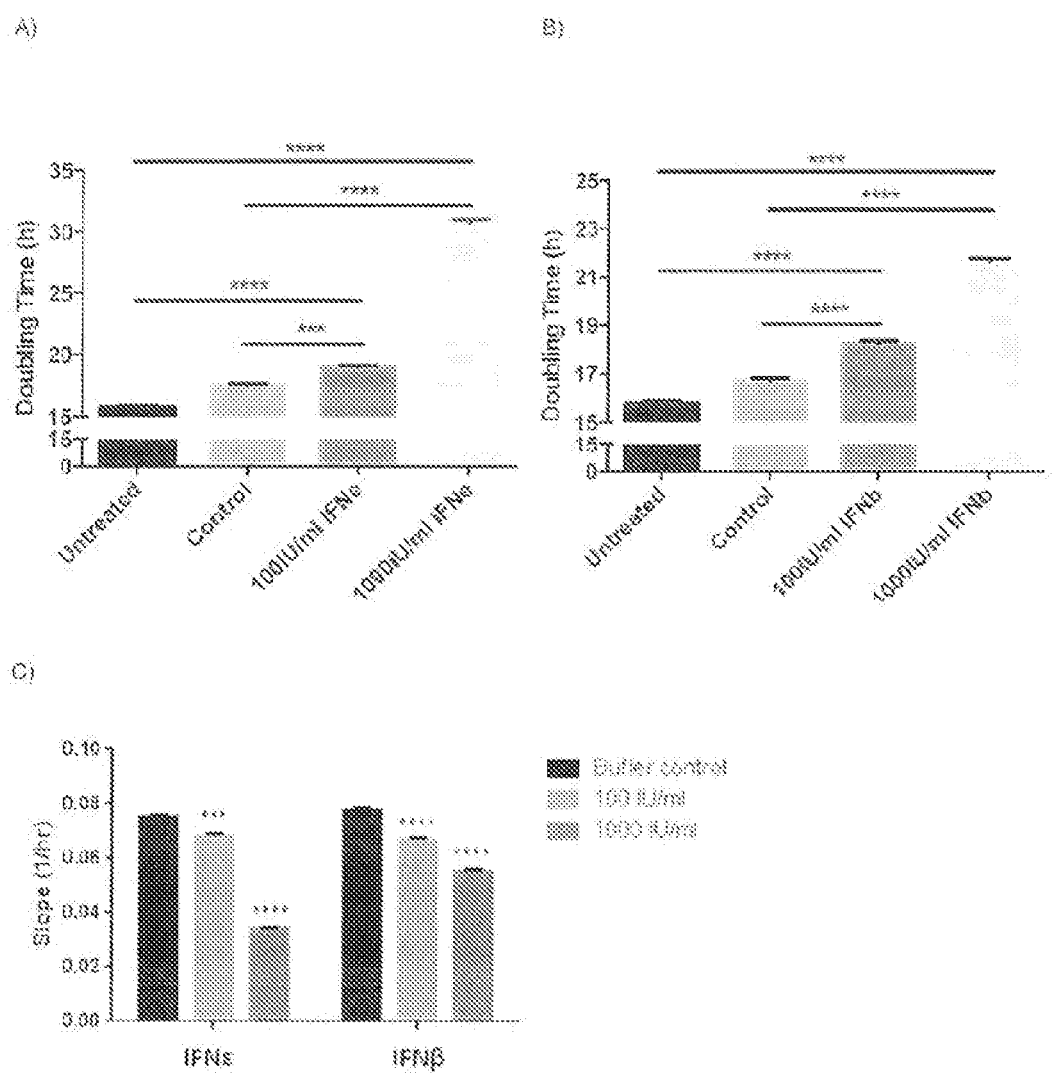
FIGS. 4A through C are graphical representations showing IFN induced inhibition of ID8 cell growth. ID8 cells were plated onto a 96 well E plate coated with electrodes to measure cell impedance. Cells were serum starved for 24 h then treated with 0-1000 IU/ml of either: (A) IFNε; or (B) IFNβ for 48 h. The cell index (CI—a measurement of impedance) was normalized to time of treatment and doubling time was calculated over 48 h post treatment using the RTCA software. (C) the slope (representative of rate of proliferation) of the growth curves was also calculated from normalized CI to 48 h post treatment using the RTCA software. Data representative of n=3 independent experiments done in technical quadruplicate. Data are expressed as mean +SD of N=3 independent experiments, analyzed using 2-way ANOVA with Sidak's multiple comparisons test, ****p,<0.0001.

From this software, this decrease can quantify cellular proliferation using two different measurements: (i) doubling time of the cells; and (ii) the slope of the growth curves of the cells indicative of growth rate. It was found that IFNε treatment increased the doubling time of ID8 cells in a dose dependent manner, similar to what was observed for IFNβ (FIGS. 4A and 4B). Also observed was a decrease in the slope of the growth curves of ID8 cells following treatment with IFNε or IFNβ (FIG. 4C). Therefore, IFNε treatment could significantly inhibit the proliferation of the murine ovarian cancer cell line.

Figure 5:
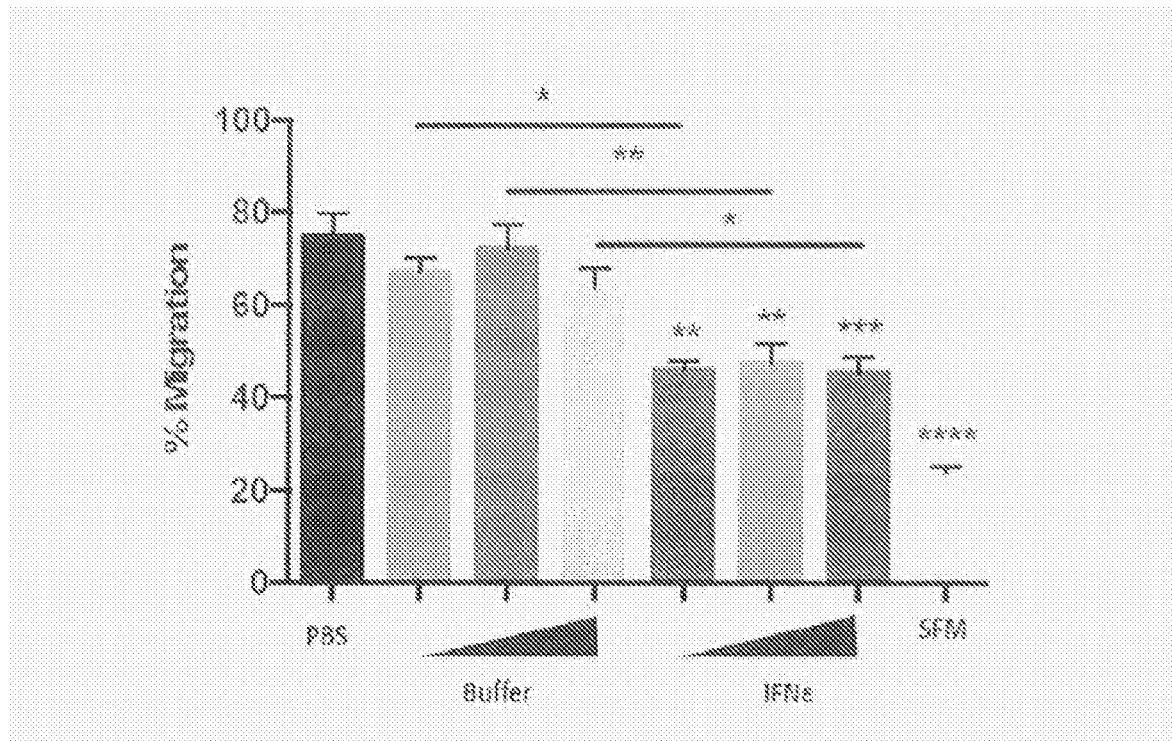
FIG. 5 is a graphical representation showing that IFNε treatment inhibits cell migration of ID8 cells. ID8 cells were treated with 1-100 IU/ml of IFNε or buffer control and migration was measured after 12 h of treatment. Fetal calf serum (FCS) was used as the chemoattractant. Serum free media (SFM) was used as a negative control. Data are representative of one independent experiment, performed in technical triplicate, and expressed as mean +SD of technical replicates. Significance was determined using a one-way ANOVA with Tukey's multiple comparisons; *p<0.05; p,0.01; *p<0.001; ****p<,0.0001.

Having observed that IFNε treatment could decrease the proliferation of ID8 cell line, next analyzed was the effect on cell migration, as an indication of how IFNε may affect metastasis of tumor cells. To do this, a fluorescent cell dye (CellTrace (Trade Mark) CSFE, ThermoFisher Scientific) was used to stain and track ID8 cell migration during a scratch assay. Using this method of analysis, the percentage migration of ID8 cells was calculated based on the closure of a 'scratch' as ID8 cells migrate from a confluent are to an open space over a 12 h period. It was found that treatment of the cells with IFNε for 12 h could significantly decrease the percentage scratch closure (or migration) of ID8 cells thereby demonstrating that IFNε affects the tumor-related in vitro activity of ID8 cell motility, which would have implications for the metastatic potential of these cells (FIG. 5).

Figure 6:
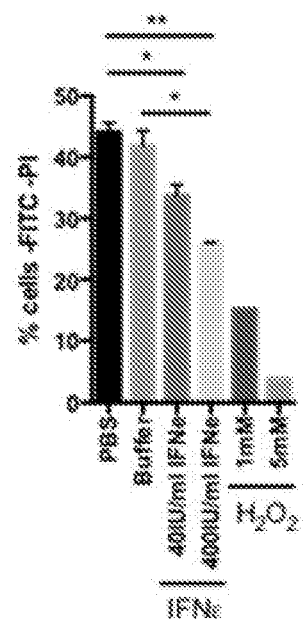
FIGS. 6A through D are graphical representations showing that IFNε treatment induces apoptosis of ID8 cells. Data show analysis of Annexin V/PI staining for ID8 cells treated with 40-400 IU/ml of IFNε for 4 hours compared to PBS and buffer treated controls. $H_2O_2$ is used as a positive control. (A) Live cells; (B) necrotic cells; (C) early apoptosis; (D) late apoptosis. Data is representative of N=3 independent experiments, performed in technical duplicate, and expressed as mean +SD of technical replicates. Significance was determined using Student's T test; *p,0.05; **p<0.01.
Figure 6:
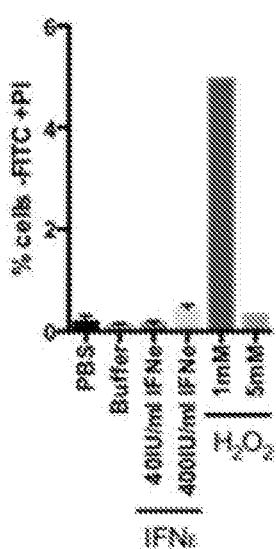
Figure 6:
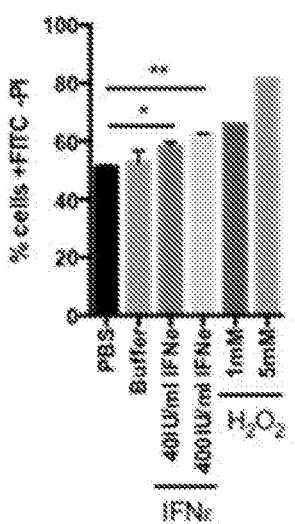
Figure 6:
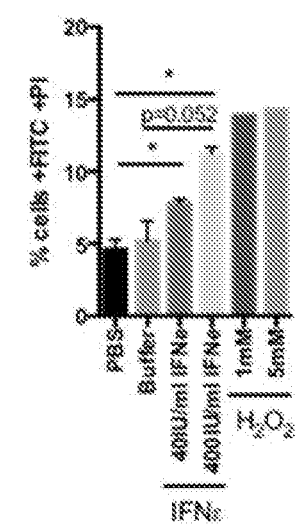

Since it was observed that IFNε inhibited ID8 cell proliferation, mobility and migration, next assessed was whether IFNε could induce apoptosis of ID8 cells. To do this, Annexin/PI staining of treated cells was used with FACS analysis to identify whether dying cells are undergoing early or late apoptosis or necrosis. It was found that IFNε treatment decreased the number of live cells by roughly 40% in the assay and upon further analysis that these cells were found to be in early and late apoptosis, as indicated by cells staining positive for both Annexin V only and both Annexin V and PI, respectively. Importantly, no necrosis was observed with any dose of IFNε assessed. The data from this FACS analysis is summarized in FIG. 6.

Example 3

The Dysregulation of IFNε in Ovarian Cancer Development: Patient Samples

IFNε expression was assayed in healthy vs ovarian cancer patients using immunohistochemistry in ovarian cancer patient samples. Tissue sections were formatted into tissue microarray (TMA) to minimize experimental error between staining. IHC analysis was commenced by staining sections from the healthy fallopian tube control samples obtained and generating control tissue blocks to stain along side the ovarian cancer patients. It was found that IFNε is highly expressed in the epithelium of the healthy fallopian tube. As controls, epithelium was stained with cytokeratin 18 and the underlying stromal cells with smooth muscle actin (SMA).

Figure 7:
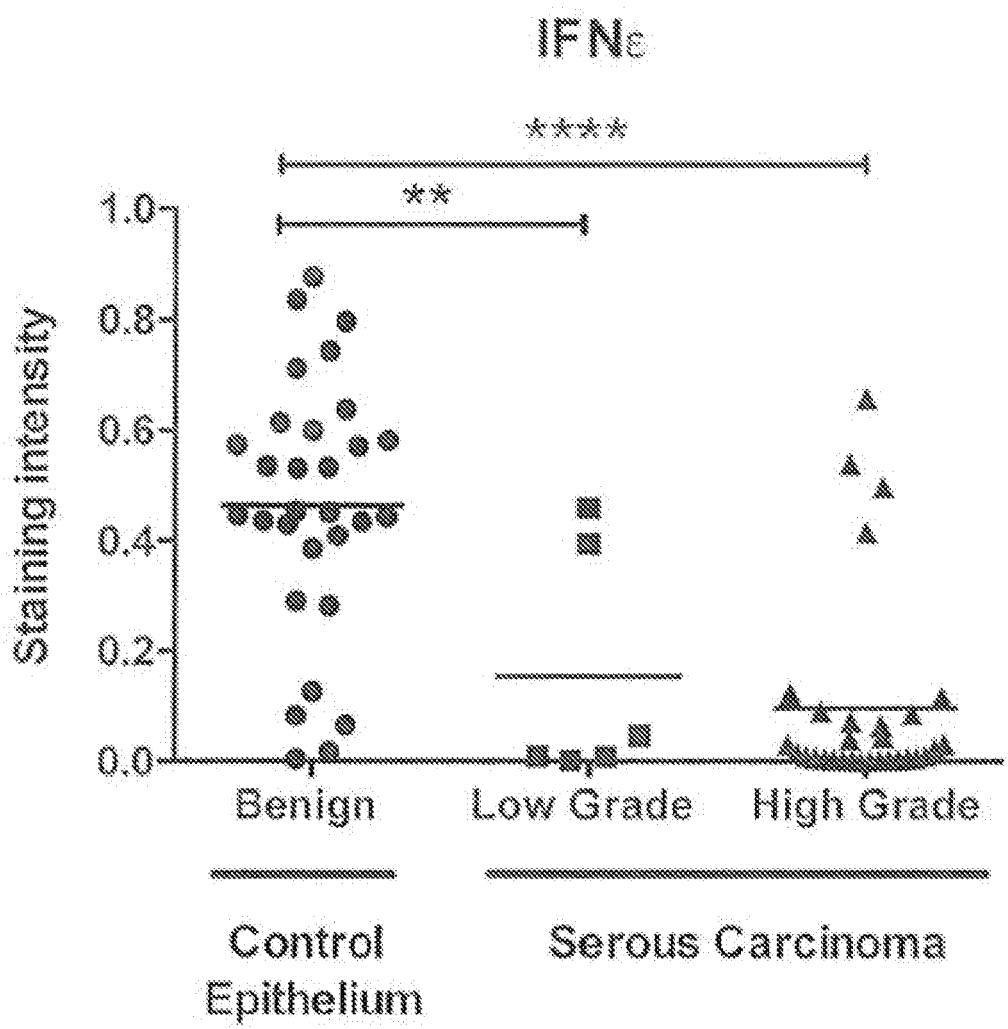
FIG. 7 is a graphical representation of IFNε staining intensity in benign human epithelium and serous carcinoma samples. Immunohistochemical staining for IFNε expression in human control epithelium low grade (LG) and high grade (HG) serous carcinoma (SC) samples were analyzed using positive pixel analysis in Imagescope software to quantify staining intensity in epithelial derived tissue components. Data are expressed as intensity scores for each sample stained in technical duplicates. Data presented as a dot plot of n=30 samples of control epithelium and epithelium from low (n=6) and high grade serous carcinoma samples (n=70), mean indicated by a bar. Data were analyzed using individual Mann-Whitney tests, p<0.01, *p<0.001.

These sections of healthy control fallopian tubes were used to generate control blocks containing up to 8 samples per block for side-by-side simultaneous staining along side ovarian cancer patient biopsy TMAs. These TMAs contain biopsies of high grade serous carcinomas, low grade serous carcinomas, benign hyperplasia and borderline epithelium from 106 patients. It was found that IFNε expression is significantly suppressed in serous carcinoma samples compared to control benign epithelium (FIG. 7).

Example 4

The Role of IFNε in Ovarian Caner Development and Therapeutic Benefit: Mouse Models The role of endogenous IFNε in tumorigenesis of ovarian cancer was investigated.

Figure 8:
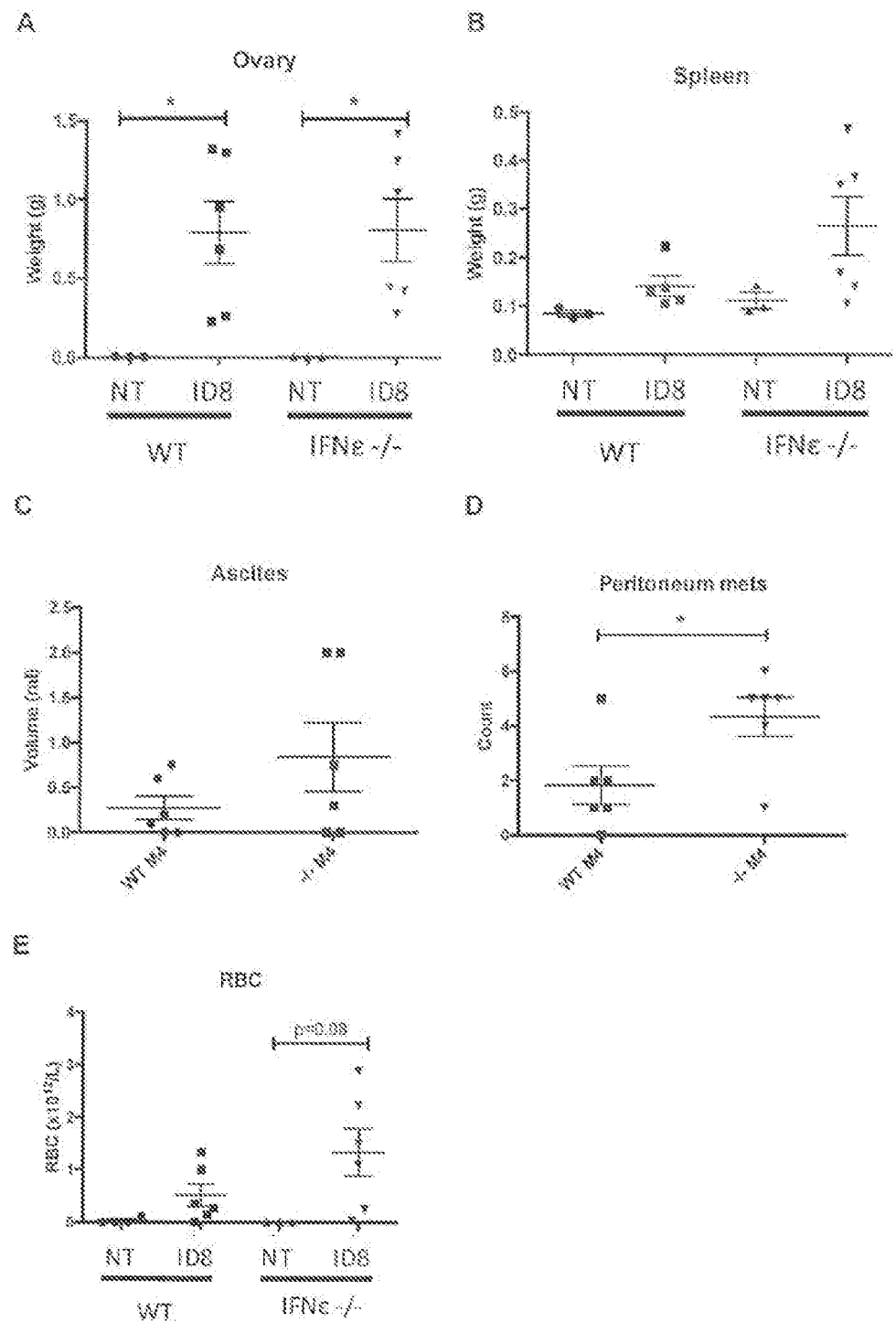
FIGS. 8A through E are graphical representations of advanced disseminated ovarian cancer metastases from orthotropic primary tumor. At 13 weeks post-intrabursal ID8 injection WT and Ifnε deficient mice demonstrate advanced primary tumors and metastatic ovarian cancer. A-B) left ovaries and spleens were weighed from non-tumor and ID8 injected mice; C) ascites fluid was drained from the peritoneum; and E) measured for red blood cell content; D) number of metastatic deposits on the peritoneal wall were recorded. Data shows n=3 non-tumor bearing and n=6 ID8 injected mice per genotype, analyzed using unpaired Student's T test *p<0.05.

C57BL/6 wild-type and Ifnε deficient mice were injected with ID8 cells into the left ovarian bursa. At 13 weeks post-injection these mice developed large orthotropic tumors and characteristic hemorrhagic ascites in the peritoneum associated with metastatic deposits on the peritoneal wall, diaphragm, spleen and mesentery. Importantly, this model of disease spread is characteristic of the progression and metastasis of advanced human ovarian cancer. At 13 weeks these mice had developed advanced disease and subsequently, it was found no difference in primary tumor size at this time between WT and Ifn$^{-/-}$ mice (FIG. 8). Instead, a trend was observed towards more advanced disseminated disease in Ifnε deficient mice including splenomegaly (FIG. 8B), ascites volume (FIG. 8C), number of metastatic peritoneal deposits (FIG. 8D) and red blood cells in drained ascites fluid (FIG. 8E). Primary tumors and metastatic deposits were collected for immunohistochemical analysis. Hematoxylin and eosin stains demonstrated mixed glandular morphology with interspersed fibroblast-like cells and adipose tissue as well as invasion into the diaphragm and spleen. This is further analyzed using multiplexing for immune cell panels.

Example 5

Additional Data from Recombinant IFNε Therapy in a Model of Disseminated Ovarian Cancer IFNε Induces Anti-Tumor Effects in Human Ovarian Cancer Cells As it was demonstrated that IFNε has strong anti-tumor effects on a murine ovarian cancer cell line, next assessed was its effects on human ovarian cell line. As documented above, CaOV3 and OVCAR4 cells were chosen as these represent HGSC.

First, it was confirmed that these cell lines responded to type I IFN stimulation. CaOV3 and OVCAR4 cells were treated with recombinant human IFNε. IRG induction was measured after 3 h of stimulation. It was found that both cell lines responded to type I IFN stimulation, although with different IRG induction observed across the different cell lines.

It was next determined if IFNε stimulation altered the proliferation of human ovarian cancer cell lines using the xCELLigence RTCA system. It was found that human ovarian cancer cells treated with IFNε had overall significantly lower cell index plots, had an increased doubling time and the slopes of their growth curves were significantly lower. This analysis demonstrates that IFNε treatment decreased proliferation of human ovarian cancer cell lines. This anti-proliferative effect of IFNε was demonstrated in CaOV3 and OVCAR4.

Figure 9:
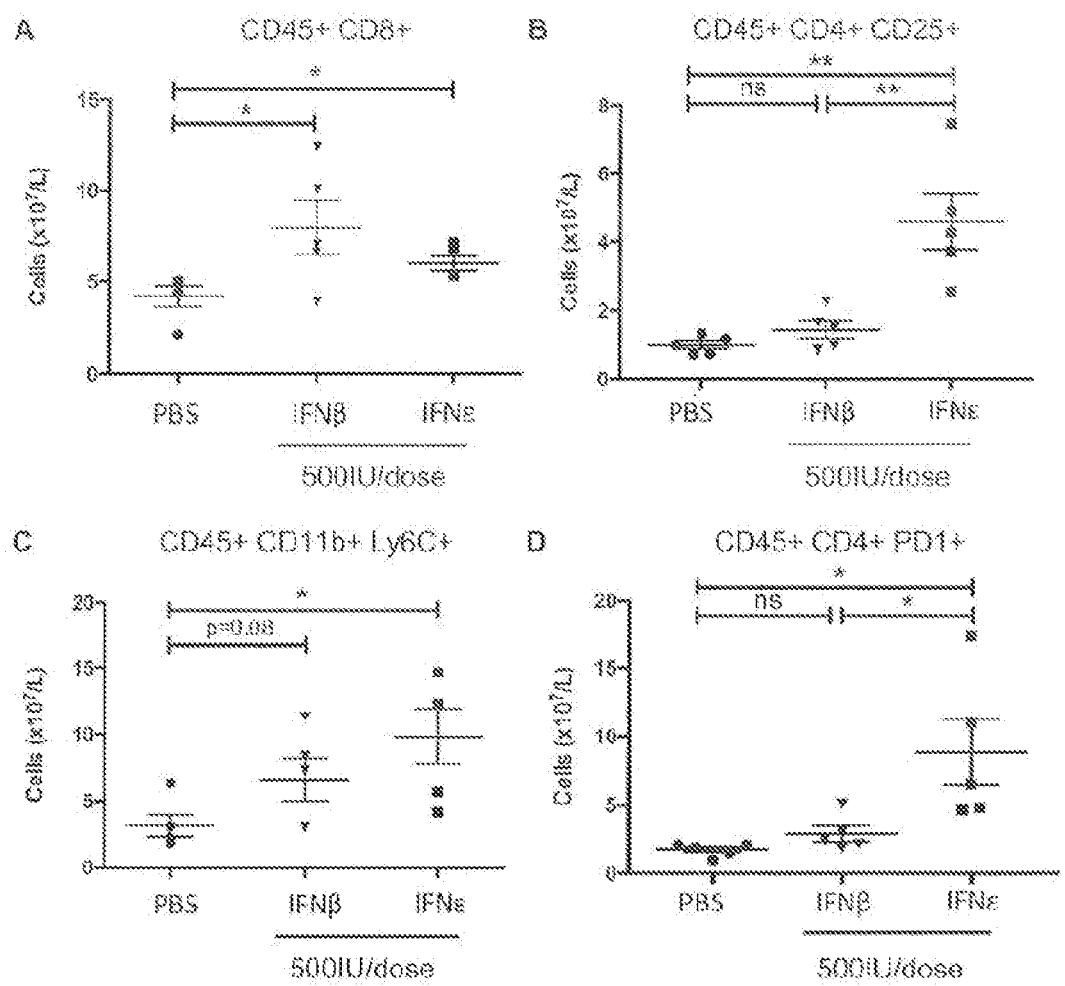
FIGS. 9A through D are graphical representations showing the recombinant IFNε regulates peritoneal immune cell populations in vivo. Healthy C57BL/6 wild-type mice (6 to 8 weeks of age) were treated with recombinant murine IFNε or IFNβ (at 500 IU/dose) via intraperitoneal injection, three times weekly for 8 weeks. Peritoneal exudate cells were collected in PBS via peritoneal lavage and analyzed using flow cytometry for immune cell populations include: A) CD45$^+$ CD8$^+$ T cells; B) CD45$^+$ CD4$^+$ T cells; C) CD45$^+$ CD11b$^+$ Ly6C+ inflammatory monocytes; and D) CD45$^+$ CD4$^+$ PD1$^+$ T cells. Data are presented as mean+/−SEM of n=5 mice per group, analyzed using unpaired Student T tests *p<0.05, **p<0.01.

Immunoregulatory Effects of Intraperitoneal Recombinant IFNε Therapy in Healthy Mice Healthy C57BL/6 wild-type mice (6 to 8 weeks of age) were treated with recombinant murine IFNε or IFNβ (at 500 IU/dose) via intraperitoneal injection, three times weekly for 8 weeks. Peritoneal exudate cells were collected in PBS via peritoneal lavage and analyzed using flow cytometry for immune cell populations. It was found that IFNε therapy significantly regulated immune cell populations known to be important in anti-cancer immunity as well las their activation status including $CD8^+$ T cells (FIG. 9A), activation of $CD4^+$ T cells (FIG. 9B), inflammatory monocytes (FIG. 9C) and PD1 expression on $CD4^+$ T cells (FIG. 9D).

Efficacy of Intraperitoneal Recombinant IFNε Therapy in a Model of Disseminated Ovarian Cancer For a model of advanced disseminated ovarian cancer that accurately recapitulates the metastatic spread (diaphragm, peritoneal wall and mesentery) malignant ascites development, splenomegaly and anemia of human ovarian cancer an intraperitoneal ID8 mouse model was used. C57BL/6 wild-type mice (6 to 8 weeks of age) were intraperitoneally injected with ID8 cells ($5 \times 10^6$ cells per mouse). At 3 days post-injection mice commenced intraperitoneal recombinant IFNε or IFNβ therapy (500 IU/dose three times weekly) for 8 weeks. It was found that mice treated with IFNε had significantly decreased tumor dissemination in the mesentery as well as fewer peritoneal and diaphragmatic deposits than PBS control mice or mice treated with IFNβ.

Figure 10:
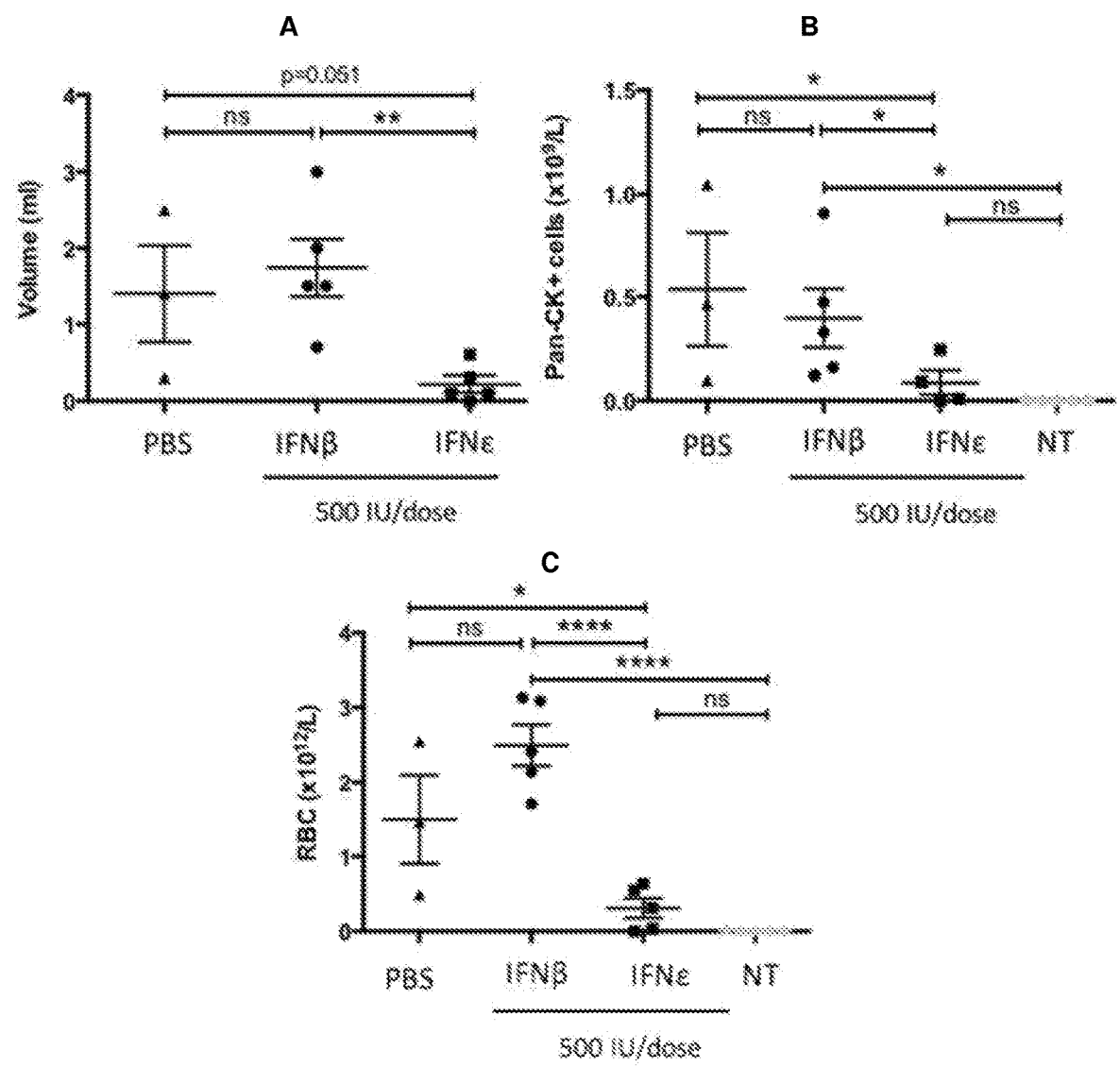
FIGS. 10A through C are graphical representations showing that IFNε suppresses malignant ascites development in a disseminated ovarian cancer model. A) image shows the volume of ascites drained from the peritoneum of mice 8 weeks post-ID8 injection treated with PBS, IFNε or IFNβ (500 IU/dose 3 times weekly); B) the number of epithelial (pan-cytokeratin positive) tumor cells in ascites fluid was measured using flow cytometry; C) the concentration of red blood cells in ascites fluid was measured using Sysmex Cell Counter. Data show n=3 PBS control mice and n=5 mice per treatment group, analyzed using unpaired Student's T test *p,0.05, p,0.01, *p<0.001.
Figure 11:
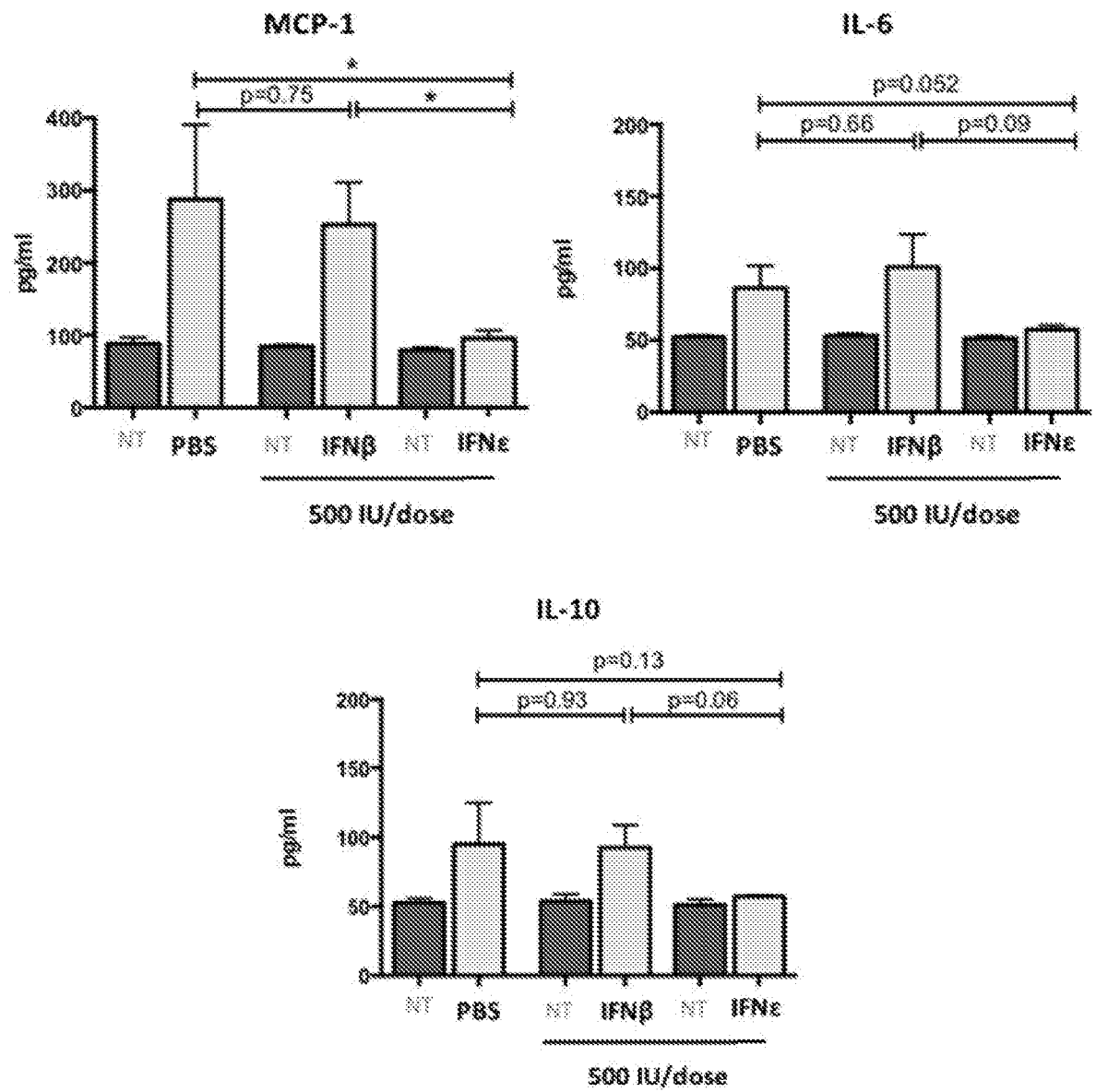
FIGS. 11A through C are graphical representations showing changes in inflammatory cytokine levels in tumor bearing mice treated with IFNε or IFNβ. Images show concentrations for MCP-1 (A), IL6 (B) and IL-10 (C) in ascites drained from the peritoneum of mice 8 weeks post-ID8 injection treated with PBS, IFNε or IFNβ (500 IU/dose 3 times weekly) measured by BD cytometric bead array (CBA). Data show are presented as mean$^{+/-}$ SEM of n=3 PBS control mice and n=5 mice per treatment group, analyzed using unpaired Student T test *p,<0.05.
Figure 12:
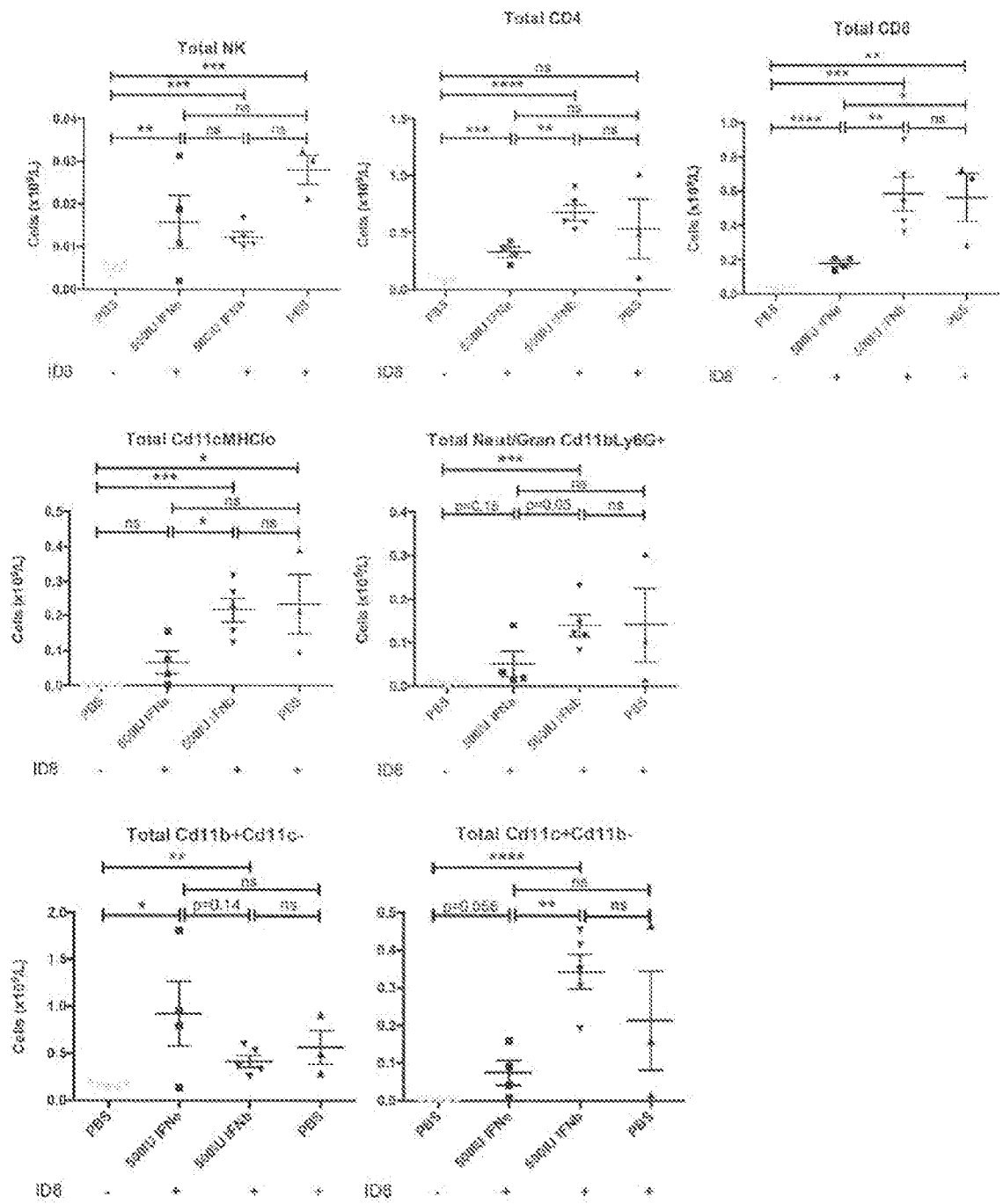
FIG. 12 is a graphical representation showing that recombinant IFNε regulates peritoneal immune cell populations in a disseminated ovarian cancer model. C57BL/6 wild-type mice (6 to 8 weeks of age) were injected intraperitoneally with ID8 cells and treated with recombinant murine IFNε or IFNβ (at 500 IU/dose) via intraperitoneal injection, three times weekly for 8 weeks. Peritoneal exudate cells were collected in PBS via peritoneal lavage and analyzed using flow cytometry for immune cell populations. Data presented as mean$^{+/-}$ SEM of n=5 mice per group, analyzed using unpaired Student T tests *p<0.05; **p<0.01.

Also found was that mice treated with IFNε had significantly reduced ascites development (FIG. 10A), with fewer detectable ascites tumor cells (FIG. 10B) and a decreased red blood cell content (FIG. 10C), indicative of less advanced disease. This was associated with suppressed inflammatory cytokine levels detectable in ascites fluid from these mice particularly MCP-1 (monocyte chemoattractant protein 1) [FIG. 11] known to facilitate angiogenesis in this disease. FIG. 12 provides data on the region of peritonea immune cell regulation by IFNε in a disseminated ovarian cancer model.

Figure 13:
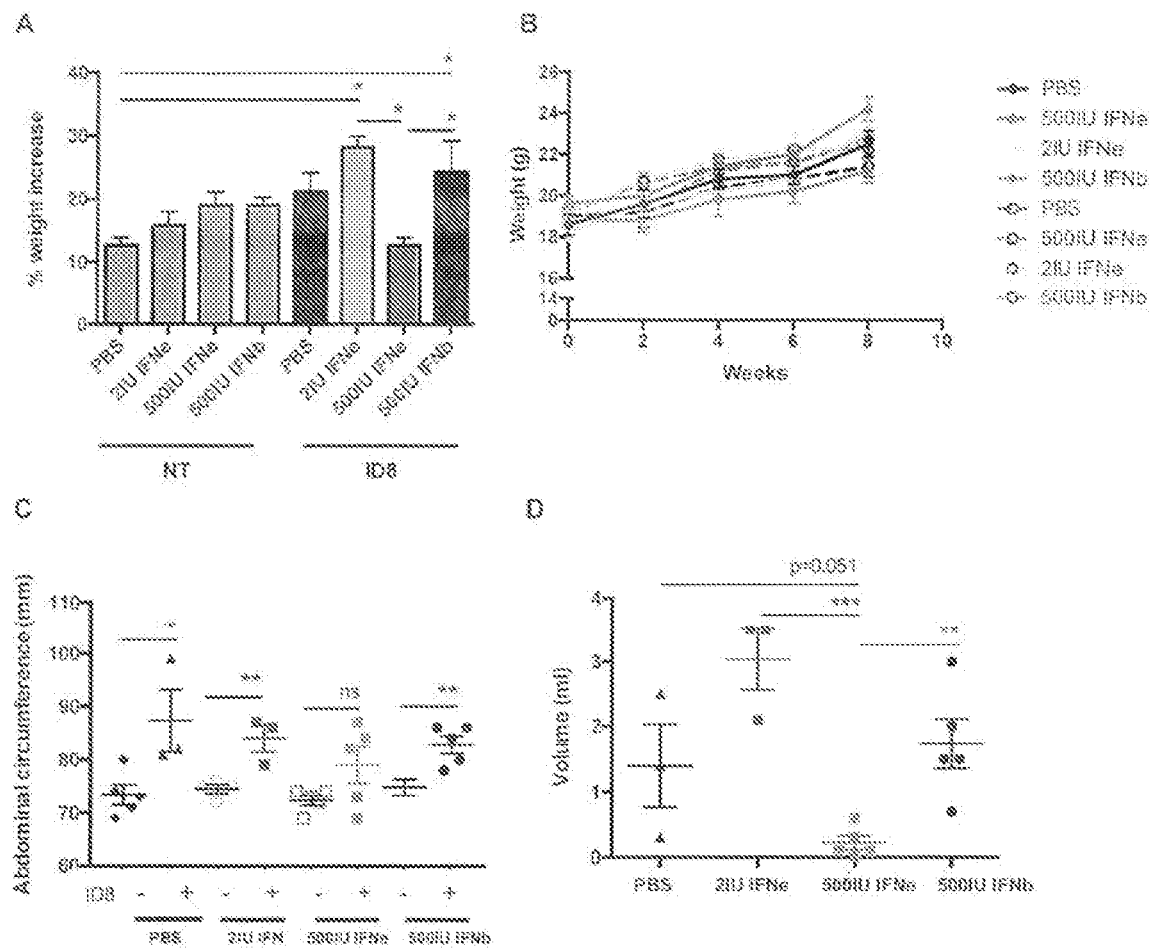
FIGS. 13A through D are graphical representations showing growth and ascites development in murine cancers of epithelial origin (EOC) treated with recombinant interferon. A) body weights of mice were monitored over 8 weeks post-ID8 cell injection and the percentage weight increase of each treatment group was calculated relative to the average of all mice on day 1, distance from the mean weight at the start of the experiment was incorporated into the overall percentage increase of each mouse. B) overall growth curves measuring total body weight of mice 8-weeks post-ID8 cell injection treated with or without recombinant IFN 3 times weekly. C) abdominal circumferences were measured at 8 weeks post-ID8 cell injection. D) total volume of ascites fluid was drained from the peritoneal cavity of each mouse 8-weeks post-ID8 cell injection. To determine significance across multiple groups an ordinary one-way ANOVA with Tukey's multiple comparisons test was performed (A) while unpaired Student T tests were used to compare two means (C and D) *p<0.001, p<0.01, *p<0.05. Data presented as mean$^{+/-}$ SEM of n=3-5 mice per group.
Figure 14:
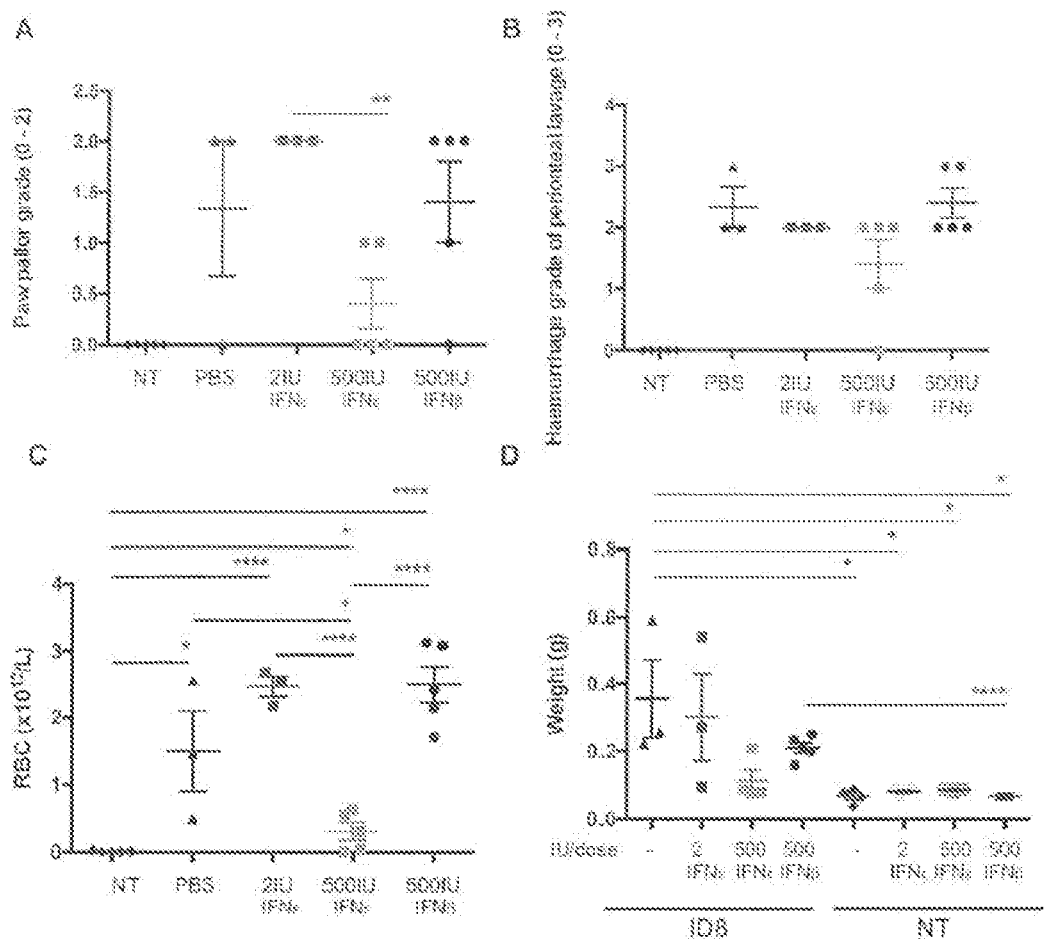
FIGS. 14A through D are graphical representations showing evidence of the effect of IFN on systemic anemia, peritoneal hemorrhaging and splenomegaly in murine EOC. A) clinical signs of anemia in mice at 8-weeks post-ID8 cell injection include pallor of the hind paws which was graded, 0—normal perfusion, 1—slight pallor, 2—extremely pale. B) peritoneal lavages were performed using 5 ml PBS and graded for hemorrhaging, 0—no hemorrhaging to 3—extensive hemorrhaging, dark red and completely opaque fluid. C) a cell count was performed on peritoneal exudate cells (PEC) including red blood cell (RBC) count. D) splenic weights from mice 8-weeks post-ID8 cell injection. Data presented as mean$^{+/-}$ SEM of n=3-5 mice per group. Significance was determined using unpaired Student's T tests **p,0.0001, p<0.01, *p<0.05.
Figure 15:
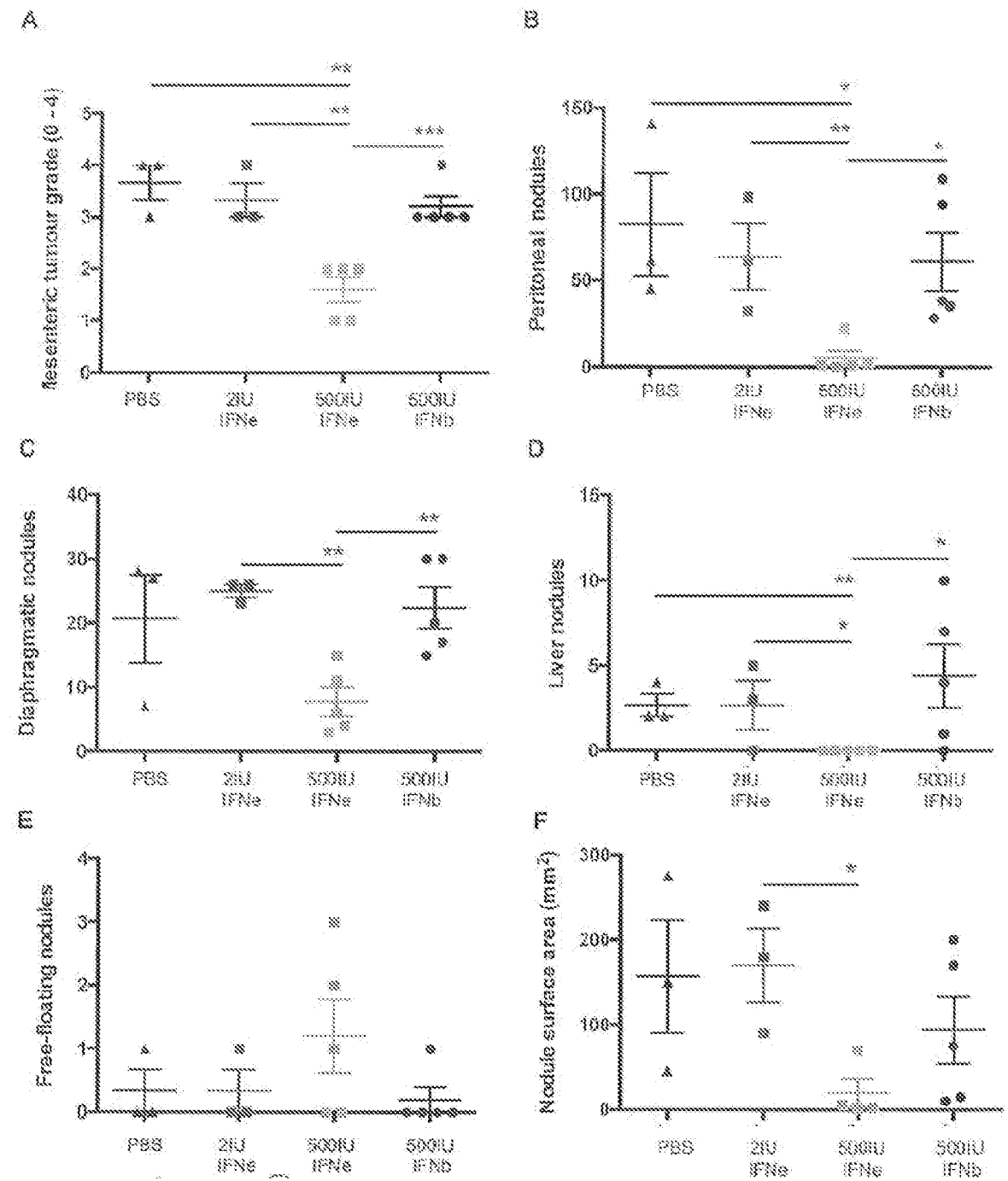
FIGS. 15A through F are graphical representations showing effects on tumor burden in murine EOC treated with recombinant IFNε. A) the extent of mesenteric tumor burden was grade, 0—no macroscopic disease to 4—extensive tumor formation evident as a large nodular sub-phrenic tumor mass as well as countless tumor deposits throughout the mesentery. B) macroscopic tumor deposits attached to the peritoneal wall were counted. These included tumors of varied sizes. C) macroscopic tumor deposits attached to the diaphragm were counted. These included tumors of varied sizes. D) macroscopic tumor deposits attached to the liver lobes were counted. E) free-floating spheroids were counted. F) surface area measurements of the largest representative tumor nodule per mouse. Data presented as mean$^{+/-}$ SEM of n=3-5 mice per group. Significance was determined using unpaired Student T tests *p<0.001, p<0.01, *p<0.05.

The results are shown in FIGS. 13 to 15.

FIG. 13

FIG. 13A shows that by 8 weeks this model had progressed enough for diffuse tumor development (as shown by weight gain and upon culling the mice) as well as hemorrhaging of the peritoneal fluid, however, this time point caught the mice just prior to advanced ascites development. None of the treatment groups showed significant weight gain difference compared to non-tumor bearing controls indicative of little ascites development. However, every treatment group except high dose IFNε are trending towards significance compared to their own control. Additionally, significant differences can be seen between tumor-bearing treatment groups, showing the least amount of disease development in mice treated with 500 IU IFNε.

FIG. 13B, significantly steeper curves can be seen in the final 2 weeks (week 6 to week 8). This time point represents progression of the disease just prior to advanced ascites development. Only mice treated with high does IFNε do not demonstrate a steeper growth rate than their non-tumor bearing controls in this period.

FIG. 13C, none of the tumor-bearing mice showed significant differences across treatment groups, however, all of the treatment groups had significantly larger circumferences compared to their non-tumor bearing controls except mice treated with high dose IFNε. This trend is somewhat reflected by the drained ascites volumes.

FIG. 13D, shows the volume of ascites fluid drained from the peritoneal cavity of each mice at the experimental endpoint of 8 weeks. Mice treated with high does IFNε constituted the only treatment group with significantly reduced ascites development (individual Mann-Whitney tests) and the only treatment group with tumor-bearing mice that had not yet developed ascites. All other tumor-bearing mice had started to develop ascites with the largest volume recorded from the low dose IFNε group (~3.5 ml). At 8 weeks these mice are still in the early stages of ascites development.

FIG. 14

Assessment of impact of tumor and IFN treatment on body weight, and several assessments of anemia (paw pallor, red blood cell counts and hemorrhage grade in Ascites fluids. Only high dose IFN had a significant effect on Paw pallor and RBC counts.

FIG. 15

FIG. 15A shows the extent of tumor development and spread throughout the mesentery graded 0 to 4 (0—no disease, 1—very little obvious disease, some small tumor deposits upon exploration, 2—obvious tumor but mainly localized to one deposit, 3—large tumor nodule developed near spleen and some deposits throughout mesentery, 4—large tumor nodule near spleen extending throughout the mesentery too numerous to count). Mice treated with high dose IFNε were the only treatment group with significantly less disease present in the mesenteric region.

FIG. 15B, mice treated with high dose IFNε had the least peritoneal nodules.

FIG. 15C, mice treated with high dose IFNε had the least diaphragmatic nodules, however, some variability in the PBS control mice prevented significance for this group.

FIG. 15D, liver nodules were not as detectable as other sites (peritoneum, diaphragm), however, there is still a trend for a reduction in mice treated with high does IFNε.

FIG. 15E is an early time point for the model by which the tumor had not had a chance to successfully adhere and colonize secondary sites. In the second model (which ran for 10 weeks with extensive ascites development), no spheroids were detected. As such spheroids may serve as a marker of less advanced disease in this model. In this current model, very few of these nodules were detected due to the reasonably advanced stage at 8 weeks (however, still earlier than last time) and while not significant, mice treated with high dose IFNε are showing the highest prevalence of non-attached spheroids. Perhaps another indicator of how IFNε may prevent the progression of this disease.

FIG. 15F, given the varying size of some of the tumor deposits the surface area dimensions were measured of the largest single tumor nodule per mouse to see whether this would still reflect a trend towards IFNε disrupting tumor growth. While there was some variability in the PBS controls (p=0.06 with high dose IFNε) high dose IFNε significantly reduced the larges nodule compared to low dose IFNε demonstrating a dose reduction in tumor growth.

Example 6

Reduced Expression of Fallopian Tube Epithelial IFN in High Grade Serous Ovarian Cancer Correlations with Poor Prognosis To further identify the potential role of IFN in ovarian cancer, its endogenous was characterized expression in human fallopian tube (FT) epithelium which contains secretory epithelial cells (SEC), which are the putative cells of origin of many HGSCs (Kurman, and Shih (2011) *Human pathology* 42:918-931). Using immunohistochemistry, the inventors showed IFNε expression in apparently all epithelia including the SEC. This expression pattern is similar to that of an epithelial marker, cytokeratin 18 and contrasted with smooth muscle actin (SMa), which stained predominately non-epithelial tissue. This expression was confirmed by analyzing a transcriptome dataset of human FT secretory cells and primary FT epithelium for expression of IFN, demonstrating that IFN was the only IFN highly and constitutively expressed in these cells.

This constitutive expression of IFN was significantly suppressed in human HGSCs compared to normal FT epithelium. This was demonstrated by staining of tissue microarrays for IFN which showed suppressed expression in low grade serous carcinoma (LGSC) and HGSC both qualitatively and quantitatively. Secondly, the inventors found significantly lower IFN transcript levels in the Australian Ovarian Cancer Study cohort (Patch et al. (2015) *Nature* 521:489-494) of HGSC samples from 93 patients. Other type I IFNs such as IFN were essentially undetectable in normal and tumor epithelium. Thirdly, the inventors validated these findings by analyzing microarray data from an external cohort of a publically available, Cancer Science Institute Singapore Ovarian Cancer Database (Tan et al. (2015) *Oncotarget* 6:43843-43852) of 707 samples of ovarian cancer and non-tumor tissues. These analyses confirm the expression of IFNε in FT epithelium and its loss in HGSC.

To determine whether IFN expression has an impact on clinical outcome, clinical survival data were interrogated on both the HGSC AOCS cohort of 93 cases and the CSIOVDB cohort of 707 cases. It was determined that high IFN expression HGSC correlates with increased progression-free and overall survival in both cohorts. Taken together these demonstrate that IFN a unique type I IFN constitutively expressed in normal epithelium, suppressed in ovarian cancer where the lower levels correlate with poor prognosis.

Example 7

IFN has Potent Anti-Tumor Effects in a Syngeneic, Orthotopic Model of Ovarian Cancer Since the above data imply IFNε has anti-tumor properties and in the absence of any prior studies to demonstrate this, the inventors investigated IFNε activity in an in vivo, syngeneic, orthotopic model of ovarian cancer (see also Example 4). The murine ovarian cancer cells, ID8 are injected, into the intrabursal space in the ovaries of immunocompetent mice (Greenaway et al. (2008) *Gynecologic oncology* 108:385-394). This model enables the assessment of the direct and indirect anti-tumor effects of IFN via tumor cell intrinsic and extrinsic (immunoregulatory) mechanisms on the 'primary' orthotopic tumor growth in the bursa and the different stages and locations of metastatic spread and growth in the peritoneal cavity.

Treatment with intraperitoneal injections of recombinant murine (rmu) IFN significantly suppressed, in a dose-dependent manner, the growth of peritoneal metastases. This was evident first in the development of malignant, hemorrhagic ascites—a key characteristic of end-stage disease in the model that closely mimics the progression of human disease. Secondly, IFN significantly reduced metastatic tumor deposits throughout the peritoneal cavity quantified as tumor burden score in the mesentery and total number of metastases throughout the peritoneum. Thirdly, IFN also reduced hemorrhaging in the peritoneal cavity, another indication of advanced stage disease. Interestingly, despite marked reduction of tumor spread, IFN had little effect on orthotopic, primary tumor growth with only a slight reduction in primary tumor size or weight, which did not reach significance. These results constitute the first demonstration that IFN clearly has anti-tumor actions and that these are against ovarian cancer metastases.

Since conventional type I IFNs can exert their anti-tumor actions via immune cell recruitment and activation, IFNε induction of these parameters was investigated in this model. Tumor bearing mice had increased numbers and proportions of total leukocytes, $CD4^+$, $CD8^+$ and B lymphocytes as well as NK cells compared to non-tumor bearing mice (NT). A manual correlation of all parameters of 'primary' and metastatic tumor burden and responses of immune cells highlighted that this immunogenic tumor model triggered host defences, marked by elevated levels of immune cells that strongly correlated with disease progression in the model. Crucially, while total immune cell numbers reflected more the presence of disease rather than differences between treatment groups, mice treated with IFN had significantly higher proportions of activated immune cells and expression of checkpoint molecules, demonstrated by induction of CD69 and PD-1 on $CD4^+$ T cells, $CD8^+$ T cells, NK cells and B cells. Indeed, disease suppression by IFNε correlated with activation of certain cell types, including $CD4^+CD69^+PD1^+$ T cells and $B220^+CD69^+$ B cells. These results show that tumor elicits a significant immune cell recruitment, but these immune cells appear not to be effective at clearing tumor burden unless activated by IFN treatment. Thus, the inventors demonstrate for the first time, that the novel type I IFNε has potent anti-tumor and immune activation activity in vivo.

In order to demonstrate the anti-tumor actions of IFNε in a more clinically relevant setting, the inventors examined its activity on an established tumor and compared activity to a conventional type I IFN, IFN. Remarkably, delaying onset of IFN treatment by 4 weeks (to allow more established orthotopic tumors to form) did not diminish overall IFN efficacy. Delayed-onset IFN therapy suppressed peritoneal spread of ovarian cancer as evident from mesenteric tumor burden, peritoneal hemorrhaging and overall metastatic score; but was ineffective at suppressing orthotopic 'primary' tumor development. In contrast, mice receiving delayed-onset IFN therapy did not exhibit reduced primary or peritoneal tumor burden. Strikingly, IFN treatment was also significantly more effective than IFN at activating the majority of peritoneal immune populations, inducing CD69 and or the checkpoint molecule, PD1 on $CD4^+$ and $CD8^+$ T cells and B cells, whereas both IFNs significantly activated NK cells.

Thus, IFNε demonstrates anti-tumor activity on the peritoneal spread of both developing and established ovarian cancer, more so than equivalent units of IFN; and furthermore, IFNε activates immune cells including CD4 and CD8 T cells and NK cells and expression of checkpoint markers.

Example 8

IFN Suppresses Ascites and Metastasis in a Model of Advanced Ovarian Cancer

Since the vast majority of HGSCs present as late-stage metastatic disease, the efficacy of exogenous IFN treatment was assessed in a model recapitulating this advanced disease by injecting ID8 cells directly into the peritoneum. Mice displayed extensive disseminated tumor growth throughout the peritoneum, with adhesions and growth of tumor nodules on multiple organs mimicking the characteristic spread of ovarian cancer in humans such as to the peritoneal wall, throughout the mesentery and on the diaphragm as well as hemorrhagic malignant ascites. Treatment with IFN significantly suppressed peritoneal tumor dissemination in this model with reduced tumor growth in the mesentery and fewer tumor nodules adhered to diaphragm and peritoneal wall. Additionally, IFN treated mice showed reduced malignant ascites development whereby peritoneal fluid was reduced in volume, markedly less hemorrhagic, and contained fewer circulating epithelial tumor cells. IFNε treatment resulted in lower levels of inflammatory cytokine levels, such as the chemokine MCP1 (CCL2). Strikingly, administration of IFN had no effect on ascites tumor growth by any measure.

The inventors found that in this advanced tumor model, total immune cells such as leukocytes, $CD4^+$ and $CD8^+$ T cells correlated with the presence of advanced disease in mice injected i/p. with ovarian tumor cells, but that these populations did not differ between treatment groups. However, IFN treatment significantly increased the proportion of activated $CD4^+$ and $CD8^+$ cells in the peritoneum of these mice typified by CD25 or CD69 and PD1 induction on CD4 T cells and CD8 T cells, which correlated with decreases in overall tumor burden and ascites development.

Example 9

Endogenous and Exogenous IFN Regulate Immune Cells In Vivo

Together the above results demonstrate that IFN maintains efficacy against peritoneal spread of developing, established and advanced models of ovarian cancer, however the mechanism of action, specific to IFNε not shared with IFN, was unknown. Since conventional type I IFNs can exert anti-tumor actions either directly on tumor cells or indirectly via immune cells, the inventors sought to define the hitherto unknown, intrinsic, in vivo immunomodulatory effects of IFN, independently of the presence of a tumor, but in the peritoneal cavity, the site of ovarian cancer metastasis. IFN treatment did not regulate $CD4^+$ T cell numbers and showed only a small but significant increase in $CD8^+CD4^-$ cells but did activate CD4 cell expression of PD1, CD69 and CD25. IFN treatment also increased total peritoneal leukocytes, inflammatory macrophages and dendritic cells.

It was next determined whether endogenous IFNε regulated immune cells in the peritoneum which could impact on tumor development at this site, by comparing WT and IFNε-/- mice. While there was no significant difference in the number of peritoneal leukocytes or total T cells, in $IFN^{-/-}$ compared to WT mice, consistent with data above, there were fewer NK cells. Furthermore, there were increased levels of activated cells including NK, and CD4T cells expressing CD69 and or PD1, which were lower in the IFNε null mice. These results show that endogenous IFNε maintains the levels and activation status of certain peritoneal immune cells, suitable for immune surveillance.

Example 10

Endogenous IFN Suppresses Ovarian Cancer Metastases

It was investigated whether endogenous IFN played a role in tumorigenesis by comparing orthotopic tumor development and dissemination in WT and $IFN^{-/-}$ mice. By 13 weeks post-ID8 implantation, $IFN^{-/-}$ mice developed peritoneal hemorrhaging and ascites accumulation, large nodular orthotopic tumors and multiple metastatic tumor deposits throughout the peritoneal cavity. Strikingly, tumor cells disseminated throughout the peritoneum more readily in the absence of endogenous IFN as shown by increased peritoneal metastases by all three measures, whereas the 'primary' orthotopic tumor growth was similar in WT and $IFN^{-/-}$ mice as demonstrated by similar ovarian weight. To gain insight into the effect of this endogenous IFN in early tumor development, the inventors compared tumor burden in mice 6 weeks post-ID8 implantation at which time, $IFN^{-/-}$ mice developed relatively small, less nodular orthotopic tumors. However, although the inventors showed there was no significant difference in primary tumor weight between WT and IFN-/-mice at this early stage, it was demonstrated an increase in tumor dissemination and metastatic growth in $IFN^{-/-}$ mice, as measured by increased tumor metastases on the peritoneal wall and total metastases found in the peritoneal cavity.

At 6 weeks post-tumor implantation, $IFN^{-/-}$ mice had increased numbers of total leukocytes, CD4 and CD8 lymphocytes compared to their non-tumor bearing (NT) genotype controls, an increase which was not seen in WT mice. The data indicate that a combination of the presence of a tumor plus the absence of suppressive signals from endogenous IFNε, resulted in increased tumor growth. Importantly, $IFN^{-/-}$ mice had significantly lower proportions of activated immune cells than WT mice demonstrated by markers expressed on CD4 and CD8 T cells including CD69 as well as PD1. These data demonstrate that although there is no significant effect of the absence of endogenous IFN at the site of tumor cell implantation, endogenous IFN signaling does influence the activation state of immune cells and suppresses the tumor-elicited influx of immune cells. These differences conferred by endogenous IFN signaling have a significant impact on the ability of tumor cells to disseminate throughout the peritoneum and establish macro-metastases on peritoneal tissues.

Example 11

Differentiating Direct and Indirect Anti-Tumor Effects of IFNε on Peritoneal Metastases In order to further dissect the mechanism of action of exogenous and endogenous IFN in the ovarian cancer models, the inventors characterized tumor development in mice lacking IFNAR1 (Ifnar1$^{-/-}$ mice), where the immune cells cannot respond to type I IFN. At 8 weeks post-ID8 injection, Ifnar1$^{-/-}$ mice demonstrated characteristic peritoneal hemorrhaging, ascites accumulation and nodular tumor deposits throughout the mesentery and adhered to the peritoneal wall. There were several indications of more advanced disease in tumor-bearing Ifnar1$^{-/-}$ mice relative to WT mice, in particular, a larger number of epithelial peritoneal tumor cells, total peritoneal leukocytes, CD4 and CD8 cells. In addition, there were trends towards increases in ascites volume and peritoneal hemorrhage.

Crucially, exogenous IFNε significantly suppressed overall tumor metastatic burden in Ifnar1$^{-/-}$ mice. Consistent with previous data, the proportion of activated cells such as CD69 positive CD4 cells and B220 positive cells was not affected indicating that this is a direct effect of IFNε. By contrast, the numbers of CD4, CD8 cells were still reduced by exogenous IFNε in the Ifnar1$^{-/-}$ mice, indicating that this effect occurs via the tumor cells (the only IFN responsive cells present)—consistent with data generated above showing indirect immunoregulatory role of exogenous IFNε on the levels of anti-tumor immune cells.

Overall these results indicate that first, endogenous IFN signaling via IFNAR1, likely by IFNε, suppresses tumor development. Secondly, the anti-tumor efficacy of exogenous IFN treatment is still evident in Ifnar1 null mice indicating a direct action by this IFN on tumor cells.

Example 12

IFN Regulates Intrinsic Anti-Tumor Activities on Ovarian Cancer Cells

While the mechanism of IFN-driven tumor suppression in this model is suggested to be via direct, tumor intrinsic mechanisms, these had not been demonstrated for this IFN. Therefore, the inventors sought to define the repertoire of direct anti-tumor effects of IFN in vitro in the mouse ovarian cancer cell line ID8. Treatment of ID8 cells with rmuIFN significantly regulated expression of genes involved in cancer-related biological pathways including immune response, PDL1, Tap1; cell death, Casp1 and Bcl-2; cell cycle, Ccne1 and Cdc20 and chemotaxis, Cxcl10. Recombinant muIFN exhibited a dose-dependent anti-proliferative effect as shown by diminished growth rate and prolonged doubling time measured using xCELLigence, which was further confirmed using MTT assay. Additionally, rmuIFN induced of increased apoptosis in these cells as demonstrated by increased Annexin V/PI staining. Collectively, the results demonstrate that murine ovarian cancer cells respond to direct stimulation with recombinant IFN through classical IFN signaling pathways including induction of IRGs involved in cancer-related pathways. Regulation of such pathways also correlates with functional assays demonstrating that in vitro, IFN has intrinsic anti-cancer properties including anti-proliferative and pro-apoptotic effects, which may therefore, be one of its mechanisms of action in vivo, consistent with the results from Ifnar null mice presented above.

In order to consolidate that these indications from the mouse model were relevant to human ovarian cancers, and given the strong clinical indications for a tumor suppressive role for IFNε in women with ovarian cancer, and in the absence of published data on the anti-tumor properties of this relatively new cytokine, the inventors tested its direct anti-tumor effects on human ovarian cancer cell lines. Recombinant human IFN (rhIFN) was used on two human ovarian cancer cell lines, CaOV3 and OVCAR4, shown previously to be representative of human HGSC (Domcke et al. (2013) supra). First, the inventors showed that these cells were directly responsive to rhIFN stimulation, which elicited a dose-dependent induction of classical IRGs such as ISG15 and IFIT1, as did IFN. Accordingly, since these data showed that rhIFN exerted classical type I IFN signaling, the inventors determined the anti-tumor effects using functional assays; the results showed that rhIFN regulated cellular proliferation and directly suppress human ovarian cancer cell growth. IFN had significant dose-dependent anti-proliferative effects on both cell lines over 48 and 72 hours as measured by doubling times. These results indicate that IFN may prolong survival in HGSC by regulating tumor cell intrinsic pathways as indicated in the preclinical animal models.

Example 13

Summary of Examples 1 to 12

Interferon epsilon (IFNε) is a type I IFN encoded by a gene in the type I IFN cluster, signaling via conventional IFNAR receptors, uniquely regulated and important in protecting the female reproductive tract (FRT) from infection.

The context of IFNε's role in the suppression of ovarian cancer is unique. It is unlike conventional type I IFNs (IFNα, IFNβ, etc. which have proven unsuccessful in ovarian cancer therapy and are not effective in the current studies) which are typical acute phase proteins, induced by danger signals and transiently expressed to be effective yet avoid potential toxicity due to excessive or sustained presence. IFNε is constitutively and constantly expressed in the FRT epithelium, not regulated by danger signals but by hormones and other 'developmental' factors. The inventors demonstrate in Examples 1 to 12, combining human and preclinical animal models, the first evidence of IFNε suppression of cancer and in particular high grade serous ovarian cancer (HGSC).

Evidence is obtained of IFNε involvement in these cancers showing:

(1) IFNε was expressed in putative cells of origin of HGSC in the Fallopian Tube epithelium;

(2) IFNε expression was reduced in HGSC;

(3) reduced IFNε expression correlated with poor prognosis.

Syngeneic, orthotopic murine models are used to define IFNε anti-tumor actions in immunocompetent mice and enabling genetic approaches to characterize mechanism of action, and complemented by studies in mouse and human ovarian cancer cell lines, demonstrating:

(4) loss of IFNε in IFNε−/− mice led to increased tumor development;

(5) mechanistically, using IFNAR1 deficient mice, the inventors showed IFNε acted directly action on tumor cells and in vitro studies showed IFNε inhibited proliferation, induced apoptosis and induced immunoregulatory surface molecules like PDL1 and chemokine expression;

(6) IFNε was particularly effective in suppression peritoneal metastases (a major problem in women with this disease);

(7) anti-tumor actions on developing, established and advanced cancers (therapeutic potential;

(8) IFNε modulates peritoneal immune cell activation and expression of PDL1 (thus combination with immunotherapy).

Thus, the inventors demonstrate that this distinct IFN has a previously unknown role in the suppression of ovarian cancer progression. Its lowered levels of expression correlate with poor prognosis and indicate a case for IFNε therapy, the potential of which is confirmed by the preclinical model studies where it inhibited cancers with developing, established and advanced peritoneal metastases. The unique properties of IFNε render it fit for purpose as an endogenous suppressor of FRT cancers. Furthermore, the induction of PDL1 on tumor cells by IFNε indicate its potential in combined therapy with checkpoint inhibition.

Example 14

Expression and Physiochemical Characterization of Recombiant Murine Human (rm)IFNε and Human (hu)IFNε

To characterize the physicochemical and biological properties of IFN, it was essential to elucidate where the signal peptide of this protein was cleaved to generate the mature, secreted protein, as is the case with previously characterized type I IFNs. The Ifne1 gene was expressed under the control of a CMV promoter and transiently transfected into HEK293 cells. Supernatants from these cells were found to contain a protein of approximately 20 kDa detected by SDS PAGE and immunoblotting with an anti-IFN monoclonal antibody. Immunoprecipitation of IFN from these supernatants led to the visualization of a band at ~20 kDa on Coomassie stained SDS-PAGE, which was not seen when immunoprecipitation was carried out with an isotype control antibody. Amino-terminal sequencing of this 20 kDa protein identified six amino acid residues 'LEPKRI (SEQ ID NO:33)', representing residues 22-27 of the rmIFN protein (Accession number NP_796322). This result indicated that the mature IFN polypeptide began at Leucine 22 of the published sequence for rmIFN (Accession number NP_796322) and therefore that the mature protein has a theoretical molecular weight of 20,006 Da (Gasteiger et al. (2003) *Nucleic Acids Res* 31:3784-3788).

For physicochemical and biological characterization rmIFN was produced in a baculovirus expression system and purified using immunoaffinity chromatography column coupled with an anti-IFN monoclonal antibody (Stifter et al. (2014) supra). Analysis of the purified protein by SDS-PAGE and western blot revealed the presence of a protein at the size expected for rmIFN (~20 kDa) which was detected with an anti-IFN antibody (clone H3). The purified protein was subjected to circular dichroism (CD) spectral analysis to demonstrate the overall protein fold. The mean residue ellipticity (MRE) showed minima at 208 and 222 nm, a profile characteristic of-helical proteins such as IFN and IFN. These data indicate that the ~20 kDa protein expressed and purified from insect cell culture had an-helical fold typical of other type I IFNs.

For Surface Plasmon Resonance (SPR), mIFNAR1-ECD and rmIFN were expressed and purified from mammalian cell and insect cell culture, respectively, as previously described (Stifter et al. (2014) *Protein Expr Purif* 94:7-14); mIFNAR2-ECDC94S and rmIFN 1 were expressed and purified from mammalian cell culture also as previously described (de Weerd et al. (2013) supra). huIFNε is produced in a similar manner. All SPR experiments were carried out on a ProteOn XPR36 (Bio-Rad Labs) using a HTG chip for His-tagged proteins and TBS as the running buffer. mIFNAR1-ECD and mIFNAR2-ECDC94S were immobilized to the nickel activated chip via the His-tags after dilution to 25 g/mL in TBS. All IFNs (rmIFN 1, rmIFN and rmIFN) were diluted in TBS to various concentrations ranging from 40 nM to 2 M. All data were referenced according to the manufacturer's instructions (Bio-Rad) and analyzed using the Langmuir binding model. Data were considered for inclusion in the analysis only if the Chit value (the measure of error between measured and fitted values) was less than 10% of the $R_{max}$ as per the manufacturer's instructions (Bio-Rad). $K_a$ (1/Ms), $K_d$ (1/s) and $K_D$ (nM) were calculated by the ProteOn Manager software and are represented as mean (+SD) from at least triplicate experiments. Significance was determined using one-way ANOVA with Dunnett's multiple comparisons testing.

SPR was used to assess the kinetics of the interactions of rmIFN with recombinant forms of the extracellular domains (ECDs) of mIFNAR1 and/or mIFNAR2, and results compared to those obtained with other type I IFNs: rmIFN 1 or rmIFN. Results revealed that rmIFN had a lower binding affinity for mIFNAR2-ECD than rmIFN 1. The affinity of the rmIFN 1-mIFNAR2-ECD interaction was 1.68 (+0.91) nM (mean of 10 independent experiments), similar to previously published studies (Jaitin et al. (2006) *Mol Cell Biol* 26:1888-1897), while the mIFN-mIFNAR2-ECD interaction was not measurable at rmIFN concentrations of up to 2 M. These concentrations indicate rmIFN has >1,000-fold lower affinity than rmIFN 1 for this receptor. Since rmIFN has a greater affinity for mIFNAR1-ECD than does rmIFN 1 (de Weerd et al. (2013) *Nat Immunol* 14:901-907, Jaks et al. (2007) *J Mol Biol* 366:525-539), the inventors compared the binding affinity of rmIFN-mIFNAR1-ECD to that of the rmIFN-mIFNAR1-ECD interaction. The affinity of rmIFN was measured for IFNAR1-ECD to be 556+239 nM (n=9 independent experiments) and around 200-fold lower compared to the rmIFN-IFNAR1-ECD interaction at 2.45+1.41 nM (n=10 independent experiments).

Results indicate that rmIFN demonstrated lower affinity for IFNAR1 and IFNAR2 compared to other type I IFNs. Following receptor engagement, an early step in IFN signaling is activation of Signal Transducers and Activators of Transcription (STAT) proteins which enter the nucleus to bind interferon stimulated response elements (ISRE) in the promoters of interferon regulated genes (IRGs). Therefore, the inventors investigated whether the rmIFN would induce activation of STAT1 and whether STAT1 would bind ISRE- and IRGpromoter driven signalling reporters.

It was sought to determine whether rmIFNε activated STAT1 like other type I IFNs. STAT1 phosphorylation on tyrosine residue 701 was apparent after stimulation of RAW264.7 cells with as little as 3 pmol/ml of rmIFNε and was found to increase in a dose-dependent manner phosphorylation of STAT1 at 0.1 pmol/ml, a 30-fold lower dose than rmIFNβ. To investigate whether or not the kinetics of STAT1 activation were different between rmIFNε and rmIFNβ, samples were taken 5, 15, 30, 60 and 120 minutes following stimulation with 10 pmol/ml of either IFN. STAT1 phosphorylation occurred as early as 5 minutes after rmIFNε stimulation, peaking 15-30 minutes after stimulation and decreasing after 60-120 minutes. Similarly, rmIFNβ stimulation resulted in peak STAT1 phosphorylation 5 minutes after treatment and was found to decrease after 120 minutes as previously published (Darnell (1997) Science 277:1630-1635). These results demonstrate that rmIFNε can induce the rapid activation of STAT1 although a higher dose is required to achieve a similar level of activation as seen by stimulation with rmIFNβ.

The data presented herein show that IFNε has low affinity for the IFNAR2 receptor but higher for the IFNAR1 receptor. rhuIFNε is produced in *E. coli* and refolded. Full length hIFN$_{[1-190]}$ was expressed as inclusion bodies (IBs) from *E. coli* BL21 (DE3). The bacteria cells were lysed, and the IBs were isolated by centrifugation. The IBs were then washed extensively using various buffers containing Triton X-100 and urea. Thereafter, the IBs were solubilized in buffer containing guanidine-HCl. The denatured protein was refolded into a soluble form using metal-catalyzed air oxidation method. Subsequently, hIFN was purified using gel filtration. Microscale thermophoresis (MST) was also employed to determine IFNε affinity for huIFNAR2 using *E. coli* expressed huIFNε. Affinity was determined to be 8,187±839 nM compared to huIFNβ of 0.25+/−0.04 nM. This indicates a high degree of huIFNε activity. This is significant since a reduced amount of huIFNε could be administered to reduce toxicity of using IFNβ.

Those skilled in the art will appreciate that the disclosure described herein is susceptible to variations and modifications other than those specifically described. It is to be understood that the disclosure contemplates all such variations and modifications. The disclosure also enables all of the steps, features, compositions and compounds referred to or indicated in this specification, individually or collectively, and any and all combinations of any two or more of the steps or features or compositions or compounds.

BIBLIOGRAPHY

AIHW (2010) *Cancer series* 52 Cat No. CAN48
Altschul et al. (1997) *Nucl. Acids. Res.* 25:3389
Ausubel et al. (*In: Current Protocols in Molecular Biology*, John Wiley & Sons Inc. 1994-1998
Berek et al. (1985) *Cancer Res.* 45:4447-53
Berek et al. (1999) *Gynecol Oncol.* 75(1):10-4
Bowtell et al. (2010) *Nature Rev Cancer* 10(11):803-8
Bruzzone et al. (1997) *Gynecol Oncol.* 65(3):499-505
Bunin et al. (1994) *Proc. Natl. Acad. Sci. USA,* 91:4708-4712
Darnell (1997) *Science* 277:1630-1635
de Weerd et al. (2013) *Nat Immunol* 14:901-907
DeWitt et al. (1993) *Proc. Natl. Acad. Sci. USA,* 90:6909-6913
Domcke et al. (2013) *Nature Communications* 4:2126
Egleton (1997) *Peptides* 18:1431-1439
Fix (1996) *Pharm Res.* 13:1760-1764
Frasci et al. (1994) *Eur J Cancer* 30A(7):946-50
Fung et al. (2013) *Science* 339(123):1088-1092
Gasteiger et al. (2003) *Nucleic Acids Res* 31:3784-3788
Greenaway et al. (2008) *Gynecologic oncology* 108:385-394
Jaitin et al. (2006) *Mol Cell Biol* 26:1888-1897
Jaks et al. (2007) *J Mol Biol* 366:525-539
Jayson et al. (2014) *The Lancet* 284(9951):1376-88
Kobolt et al. (2012) *Nature* 490(7418):61-70
Kurman, and Shih (2011) *Human pathology* 42:918-931
Langer (1990) *Science* 249:1527-1533
Mangan et al. *Eur J Immunol*, 2007, 37(5):1302-12
Markman et al. (1992) *Gynecol Oncol.* 45(1):3-8
Markman et al. (2004) *Oncology* 66(5):343-6
Moore et al. (1995) *Gynecol Oncol.* 59(2):267-72
Patch et al. (2015) *Nature* 521:489-494
Patton (1998) *Biotechniques* 16:141-143
Peng et al. (2007) *Prot Expr Purif* 53:356-364
Putney (1998) *Nat. Biotechnol.* 16:153-157
Roby et al. (2000) *Carcinogenesis* 21(4):585-591
Salamonsen et al. *Semin Reprod Med*, 2007, 25(6):437-44
Samanen (1996) *J. Pharm. Pharmacol.* 48:119-135
Sieh et al. (2013) *The Lancet Oncology* 14(9):853-62
Smith et al. *J Immunol*, 2007, 178(7):4557-66
Stifter et al. (2014) *Protein Expr Purif* 94:7-14
Tan et al. (2015) *Oncotarget* 6:43843-43852
Thakkar and Mehta (2011) *Oncologist* 16(3):276-85
Tothill et al. (2008) *Clin Cancer Res.* 14(16):5198-208
Venkitaraman (2014) *Science* 343(6178):1470-5
Willemse et al. (1990) *Eur J Cancer Clin Oncol* 26(3):353-8

The invention claimed is:

1. A method for inhibiting replication, growth, development, motility, proliferation, survival, and/or migration of an ovarian cancer cell in a subject or of ovarian cancer metastases, said method comprising exposing the ovarian cancer cell or metastases to an amount of interferon epsilon (IFNε) effective to directly or indirectly induce apoptosis of the ovarian cancer cell or metastases, wherein the IFNε has at least 80% sequence identity to SEQ ID NO: 28 or SEQ ID NO: 32 and has INFε activity.

2. The method of claim 1, wherein the IFNε is derived from a species homologous to the species of the subject being treated.

3. The method of claim 1, wherein the IFNε is derived from a species heterologous to the species of the subject being treated.

4. The method of claim 1, wherein the subject is a human.

5. The method of claim 1, wherein the ovarian cancer cell is a low to high grade serous carcinoma cell.

6. The method of claim 1, wherein the ovarian cancer cell is a high grade serous carcinoma cell.

7. The method of claim 1, wherein the IFNε is used in combination with another anti-cancer agent.

8. The method of claim 7, wherein the anti-cancer agent is selected from the group consisting of a chemotherapeutic agent, an antimetabolite, anti-tumor antibiotic, mitotic inhibitor, steroid, sex hormone or hormone-like drug, alkylating agent, nitrogen mustard, nitrosoureas, hormone agonist and microtubular inhibitor.

9. The method of claim 1, wherein the amount of IFNε is from 10 IU/dose to $10^6$ IU/dose.

10. A method of treating a subject with ovarian cancer or ovarian cancer metastases, the method comprising administering to the subject an effective amount of IFNε to directly or indirectly induce apoptosis of an ovarian cancer cell; or inhibit replication, growth, development, motility, proliferation, survival and/or migration of a ovarian cancer cell or an ovarian cancer metastasis, wherein the IFNε has at least 80% sequence identity to SEQ ID NO: 28 or SEQ ID NO: 32 and has IFNε activity.

11. The method of claim 10, wherein the IFNε is derived from a species homologous to the species of the subject being treated.

12. The method of claim 10, wherein the IFNε is derived from a species heterologous to the species of the subject being treated.

13. The method of claim 10, wherein the subject is a human.

14. The method of claim 10, wherein the ovarian cancer cell is a low to high grade serous carcinoma cell.

15. The method of claim 10, wherein the ovarian cancer cell is a high grade serous carcinoma cell.

16. The method of claim 10, wherein the IFNε is used in combination with another anti-cancer agent.

17. The method of claim 16, wherein the anti-cancer agent is selected from the group consisting of a chemotherapeutic agent, an antimetabolite, anti-tumor antibiotic, mitotic inhibitor, steroid, sex hormone or hormone-like drug, alkylating agent, nitrogen mustard, nitrosoureas, hormone agonist and microtubular inhibitor.

18. The method of claim 10, wherein the amount of IFNε is from 10 IU/dose to $10^6$ IU/dose.

* * * * *

SEQUENCE LISTING

```
<160> NUMBER OF SEQ ID NOS: 33

<210> SEQ ID NO 1
<211> LENGTH: 21
<212> TYPE: DNA
<213> ORGANISM: artificial
<220> FEATURE:
<223> OTHER INFORMATION: 5' GAPDH primer

<400> SEQUENCE: 1
gaacgggaag cttgtcatca a                                          21

<210> SEQ ID NO 2
<211> LENGTH: 20
<212> TYPE: DNA
<213> ORGANISM: artificial
<220> FEATURE:
<223> OTHER INFORMATION: 3' GAPDH primer
```

```
<400> SEQUENCE: 2
ctaagcagtt ggtggtgcag                                               20

<210> SEQ ID NO 3
<211> LENGTH: 20
<212> TYPE: DNA
<213> ORGANISM: artificial
<220> FEATURE:
<223> OTHER INFORMATION: 5' 18S primer

<400> SEQUENCE: 3
gtaacccgtt gaaccccatt                                               20

<210> SEQ ID NO 4
<211> LENGTH: 20
<212> TYPE: DNA
<213> ORGANISM: artificial
<220> FEATURE:
<223> OTHER INFORMATION: 3' 18S primer

<400> SEQUENCE: 4
ccatccaatc ggtagtagcg                                               20

<210> SEQ ID NO 5
<211> LENGTH: 20
<212> TYPE: DNA
<213> ORGANISM: artificial
<220> FEATURE:
<223> OTHER INFORMATION: 5' Isg15 primer

<400> SEQUENCE: 5
tgagagcaag cagccagaag                                               20

<210> SEQ ID NO 6
<211> LENGTH: 20
<212> TYPE: DNA
<213> ORGANISM: artificial
<220> FEATURE:
<223> OTHER INFORMATION: 3' Isg15 primer

<400> SEQUENCE: 6
acggacacca ggaaatcgtt                                               20

<210> SEQ ID NO 7
<211> LENGTH: 20
<212> TYPE: DNA
<213> ORGANISM: artificial
<220> FEATURE:
<223> OTHER INFORMATION: 5' Tap1 primer

<400> SEQUENCE: 7
cgcaacatat ggctcatgtc                                               20

<210> SEQ ID NO 8
<211> LENGTH: 19
<212> TYPE: DNA
<213> ORGANISM: artificial
<220> FEATURE:
<223> OTHER INFORMATION: 3' Tap1 primer

<400> SEQUENCE: 8
gcccgaaaca cctctctgt                                                19

<210> SEQ ID NO 9
<211> LENGTH: 20
```

```
<212> TYPE: DNA
<213> ORGANISM: artificial
<220> FEATURE:
<223> OTHER INFORMATION: 5' Cdc20 primer

<400> SEQUENCE: 9
gtcactccgc tcgagtaagc                                            20

<210> SEQ ID NO 10
<211> LENGTH: 20
<212> TYPE: DNA
<213> ORGANISM: artificial
<220> FEATURE:
<223> OTHER INFORMATION: 3' Cdc20 primer

<400> SEQUENCE: 10
gcccacatac ttcctggcta                                            20

<210> SEQ ID NO 11
<211> LENGTH: 20
<212> TYPE: DNA
<213> ORGANISM: artificial
<220> FEATURE:
<223> OTHER INFORMATION: 5' Ccne1 primer

<400> SEQUENCE: 11
cctccaaagt tgcaccagtt                                            20

<210> SEQ ID NO 12
<211> LENGTH: 20
<212> TYPE: DNA
<213> ORGANISM: artificial
<220> FEATURE:
<223> OTHER INFORMATION: 3' Ccne1 primer

<400> SEQUENCE: 12
agagggctta gacgccactt                                            20

<210> SEQ ID NO 13
<211> LENGTH: 22
<212> TYPE: DNA
<213> ORGANISM: artificial
<220> FEATURE:
<223> OTHER INFORMATION: 5' Cxcl10 primer

<400> SEQUENCE: 13
ctgaatccgg aatctaagac ca                                         22

<210> SEQ ID NO 14
<211> LENGTH: 20
<212> TYPE: DNA
<213> ORGANISM: artificial
<220> FEATURE:
<223> OTHER INFORMATION: 3' Cxcl10 primer

<400> SEQUENCE: 14
gaggctctct gctgtccatc                                            20

<210> SEQ ID NO 15
<211> LENGTH: 20
<212> TYPE: DNA
<213> ORGANISM: artificial
<220> FEATURE:
<223> OTHER INFORMATION: 5' Ifit1 primer

<400> SEQUENCE: 15
```
tcaaggcagg tttctgagga                                              20

<210> SEQ ID NO 16
<211> LENGTH: 20
<212> TYPE: DNA
<213> ORGANISM: artificial
<220> FEATURE:
<223> OTHER INFORMATION: 3' Ifit1 primer

<400> SEQUENCE: 16
acctggtcac catcagcatt                                              20

<210> SEQ ID NO 17
<211> LENGTH: 23
<212> TYPE: DNA
<213> ORGANISM: artificial
<220> FEATURE:
<223> OTHER INFORMATION: 5' ISG15 primer

<400> SEQUENCE: 17
acgccatggc tgacaagatc ctg                                          23

<210> SEQ ID NO 18
<211> LENGTH: 22
<212> TYPE: DNA
<213> ORGANISM: artificial
<220> FEATURE:
<223> OTHER INFORMATION: 3' ISG15 primer

<400> SEQUENCE: 18
ggtcccgtgc cttgtccata gc                                           22

<210> SEQ ID NO 19
<211> LENGTH: 20
<212> TYPE: DNA
<213> ORGANISM: artificial
<220> FEATURE:
<223> OTHER INFORMATION: 5' IFIT1 primer

<400> SEQUENCE: 19
gaaacggatt cccttccaat                                              20

<210> SEQ ID NO 20
<211> LENGTH: 20
<212> TYPE: DNA
<213> ORGANISM: artificial
<220> FEATURE:
<223> OTHER INFORMATION: 3' IFIT1 primer

<400> SEQUENCE: 20
actgctggac tgacgagctt                                              20

<210> SEQ ID NO 21
<211> LENGTH: 20
<212> TYPE: DNA
<213> ORGANISM: artificial
<220> FEATURE:
<223> OTHER INFORMATION: 5' ISG15 primer

<400> SEQUENCE: 21
gcgaactcat ctttgccagt                                              20

<210> SEQ ID NO 22
<211> LENGTH: 20
<212> TYPE: DNA
<213> ORGANISM: artificial

```
<220> FEATURE:
<223> OTHER INFORMATION: 3' ISG15 primer

<400> SEQUENCE: 22
agcatcttca ccgtcaggtc                                                 20

<210> SEQ ID NO 23
<211> LENGTH: 20
<212> TYPE: DNA
<213> ORGANISM: artificial
<220> FEATURE:
<223> OTHER INFORMATION: 5' IFIT1 primer

<400> SEQUENCE: 23
agcttacacc attggctgct                                                 20

<210> SEQ ID NO 24
<211> LENGTH: 23
<212> TYPE: DNA
<213> ORGANISM: artificial
<220> FEATURE:
<223> OTHER INFORMATION: 3' IFIT1 primer

<400> SEQUENCE: 24
ccatttgtac tcatggttgc tgt                                             23

<210> SEQ ID NO 25
<211> LENGTH: 20
<212> TYPE: DNA
<213> ORGANISM: artificial
<220> FEATURE:
<223> OTHER INFORMATION: 5' IFNepsilon primer

<400> SEQUENCE: 25
aggacacact ctggccattc                                                 20

<210> SEQ ID NO 26
<211> LENGTH: 20
<212> TYPE: DNA
<213> ORGANISM: artificial
<220> FEATURE:
<223> OTHER INFORMATION: 3' IFNepsilon primer

<400> SEQUENCE: 26
ctcccaacca tccagagaaa                                                 20

<210> SEQ ID NO 27
<211> LENGTH: 581
<212> TYPE: DNA
<213> ORGANISM: artificial
<220> FEATURE:
<223> OTHER INFORMATION: hIFNepsilon

<400> SEQUENCE: 27
agatctgggt agcctggatc tgaaactgat tatctttcag cagcgtcagg ttaatcaaga     60
aagcctgaaa ctgctgaata aactgcaaac cctgagcatc cagcagtgtc tgccgcatcg    120
taaaaacttt ctgctgcctc agaaaagcct gagtccgcag cagtatcaga aaggtcatac    180
cctggcaatt ctgcatgaaa tgctgcaaca atctttagc ctgtttcgtg caaatattag     240
tctggatggt tgggaagaaa accataccga aaaatttctg attcagctgc accagcagct    300
ggaatatctg gaagcactga tgggtctgga agccgaaaaa ctgagcggca ccctgggtag    360
cgataatctg cgtctgcaag ttaaaatgta ttttcgtcgc atccacgact atctggaaaa    420
```

```
tcaggattat agcacctgtg catgggcaat tgttcaggtt gaaattagcc gttgcctgtt      480 tttttgttttt agcctgacag agaaactgag caaacagggt cgtccgctga atgatatgaa      540
acaagaactg accaccgaat tcgtagtcc  gcgttctgca g                           581
```

<210> SEQ ID NO 28
<211> LENGTH: 193
<212> TYPE: PRT
<213> ORGANISM: artificial
<220> FEATURE:
<223> OTHER INFORMATION: hIFNepsilon

<400> SEQUENCE: 28

```
Asp Leu Gly Ser Leu Asp Leu Lys Leu Ile Ile Phe Gln Gln Arg Gln
1               5                   10                  15

Val Asn Gln Glu Ser Leu Lys Leu Leu Asn Lys Leu Gln Thr Leu Ser
            20                  25                  30

Ile Gln Gln Cys Leu Pro His Arg Lys Asn Phe Leu Leu Pro Gln Lys
        35                  40                  45

Ser Leu Ser Pro Gln Gln Tyr Gln Lys Gly His Thr Leu Ala Ile Leu
    50                  55                  60

His Glu Met Leu Gln Gln Ile Phe Ser Leu Phe Arg Ala Asn Ile Ser
65                  70                  75                  80

Leu Asp Gly Trp Glu Glu Asn His Thr Glu Lys Phe Leu Ile Gln Leu
                85                  90                  95

His Gln Gln Leu Glu Tyr Leu Glu Ala Leu Met Gly Leu Glu Ala Glu
            100                 105                 110

Lys Leu Ser Gly Thr Leu Gly Ser Asp Asn Leu Arg Leu Gln Val Lys
        115                 120                 125

Met Tyr Phe Arg Arg Ile His Asp Tyr Leu Glu Asn Gln Asp Tyr Ser
    130                 135                 140

Thr Cys Ala Trp Ala Ile Val Gln Val Glu Ile Ser Arg Cys Leu Phe
145                 150                 155                 160

Phe Val Phe Ser Leu Thr Glu Lys Leu Ser Lys Gln Gly Arg Pro Leu
                165                 170                 175

Asn Asp Met Lys Gln Glu Leu Thr Thr Glu Phe Arg Ser Pro Arg Ser
            180                 185                 190

Ala
```

<210> SEQ ID NO 29
<211> LENGTH: 510
<212> TYPE: DNA
<213> ORGANISM: artificial
<220> FEATURE:
<223> OTHER INFORMATION: Tagless mIFNepsilon

<400> SEQUENCE: 29

```
ccgaaacgga ttcccttcca attgtggatg aacagagaaa gcctacaact actgaaacct      60
ttgccaagct cgtcagtcca gcagtgtcta gcacacagga agaatttcct gcttcctcag     120
cagcctgtga gtcctcacca gtaccaagag ggacaggtgc tggctgttgt gcacgagatc     180
cttcagcaga tcttcacgct cctccagaca catgggacta tgggcatttg ggaggaaaac     240
catatagaaa aagtcttagc tgcgcttcac cggcagctgg aatacgtgga gtcactgggt     300
ggactgaacg cagcgcagaa gagtgggggc tcgagtgcgc agaacctag  gttacagatt     360 aaagcatact tcaggaggat ccacgattac ttggaaaacc aaaggtacag cagctgtgcc     420
tggatcattg tccagacaga aatccaccgc tgtatgttct ttgtgttcag gttcacaaca     480
```

```
tggctgagca gacaagaccc agacccttga                                    510
```

<210> SEQ ID NO 30
<211> LENGTH: 510
<212> TYPE: DNA
<213> ORGANISM: artificial
<220> FEATURE:
<223> OTHER INFORMATION: Optim

<400> SEQUENCE: 30

```
ccaaagcgca tcccatttca gctgtggatg aaccgcgaga gcctccagct ccttaagcca    60
ctgccctcct cgtcagtgca gcagtgtctg gccaccgta agaatttcct cctcccacaa   120
cagcccgtct cacctcatca atatcaggag ggtcaagtgc tggctgtcgt gcatgagatc   180
ctgcagcaaa tcttcacact gcttcagact cacggcacta tgggtatttg ggaggagaac   240
catatcgaga aggtgctggc tgccctccat cgtcagctgg agtatgttga gcctgggga    300
ggcctaaacg ctgcccagaa gtcaggcggc tctagtgcac agaacctgcg cttgcagatc   360
aaggcttact ccgtcgcat tcacgattac ctggagaatc agcgctactc tagctgtgcc   420
tggatcatcg ttcaaaccga atccaccgt tgtatgttct cgtgttccg atttacgacc    480
tggctgtcac gccaagaccc tgacccatga                                    510
```

<210> SEQ ID NO 31
<211> LENGTH: 522
<212> TYPE: DNA
<213> ORGANISM: artificial
<220> FEATURE:
<223> OTHER INFORMATION: mIFNeplison

<400> SEQUENCE: 31

```
gccgaattgg aaccaaagcg catcccattt cagctgtgga tgaaccgcga gagcctccag    60
ctccttaagc cactgccctc ctcgtcagtg cagcagtgtc tggcccaccg taagaatttc   120
ctcctcccac aacagcccgt ctcacctcat caatatcagg agggtcaagt gctggctgtc   180
gtgcatgaga tcctgcagca aatcttcaca ctgcttcaga ctcacggcac tatgggtatt   240
tgggaggaga accatatcga gaaggtgctg gctgccctcc atcgtcagct ggagtatgtt   300
gagagcctgg gaggcctaaa cgctgcccag aagtcaggcg gctctagtgc acagaacctg   360
cgcttgcaga tcaaggctta cttccgtcgc attcacgatt acctggagaa tcagcgctac   420
tctagctgtg cctggatcat cgttcaaacc gaaatccacc gttgtatgtt cttcgtgttc   480
cgatttacga cctggctgtc acgccaagac cctgacccat ga                      522
```

<210> SEQ ID NO 32
<211> LENGTH: 173
<212> TYPE: PRT
<213> ORGANISM: artificial
<220> FEATURE:
<223> OTHER INFORMATION: mIFNeplison

<400> SEQUENCE: 32

```
Ala Glu Leu Glu Pro Lys Arg Ile Pro Phe Gln Leu Trp Met Asn Arg
1               5                   10                  15

Glu Ser Leu Gln Leu Leu Lys Pro Leu Pro Ser Ser Val Gln Gln
            20                  25                  30

Cys Leu Ala His Arg Lys Asn Phe Leu Leu Pro Gln Gln Pro Val Ser
        35                  40                  45
```

```
Pro His Gln Tyr Gln Glu Gly Gln Val Leu Ala Val Val His Glu Ile
    50                  55                  60

Leu Gln Gln Ile Phe Thr Leu Leu Gln Thr His Gly Thr Met Gly Ile
65                  70                  75                  80

Trp Glu Glu Asn His Ile Glu Lys Val Leu Ala Ala Leu His Arg Gln
                85                  90                  95

Leu Glu Tyr Val Glu Ser Leu Gly Gly Leu Asn Ala Ala Gln Lys Ser
            100                 105                 110

Gly Gly Ser Ser Ala Gln Asn Leu Arg Leu Gln Ile Lys Ala Tyr Phe
            115                 120                 125

Arg Arg Ile His Asp Tyr Leu Glu Asn Gln Arg Tyr Ser Ser Cys Ala
        130                 135                 140

Trp Ile Ile Val Gln Thr Glu Ile His Arg Cys Met Phe Phe Val Phe
145                 150                 155                 160

Arg Phe Thr Thr Trp Leu Ser Arg Gln Asp Pro Asp Pro
                165                 170

<210> SEQ ID NO 33
<211> LENGTH: 6
<212> TYPE: PRT
<213> ORGANISM: artificial
<220> FEATURE:
<223> OTHER INFORMATION: rmIFNe

<400> SEQUENCE: 33

Leu Glu Pro Lys Arg Ile
1               5
```